(12) United States Patent
Aronsen et al.

(10) Patent No.: US 11,419,874 B2
(45) Date of Patent: Aug. 23, 2022

(54) TREATMENT OF TACHYCARDIA

(71) Applicant: OSLO UNIVERSITY HOSPITAL HF, Oslo (NO)

(72) Inventors: Jan Magnus Aronsen, Oslo (NO);
Jonas Skogestad, Oslo (NO)

(73) Assignee: OSLO UNIVERSITY HOSPITAL HF, Oslo (NO)

( * ) Notice: Subject to any disclaimer, the term of this patent is extended or adjusted under 35 U.S.C. 154(b) by 0 days.

(21) Appl. No.: 16/766,388

(22) PCT Filed: Nov. 23, 2018

(86) PCT No.: PCT/EP2018/082450
§ 371 (c)(1),
(2) Date: May 22, 2020

(87) PCT Pub. No.: WO2019/101970
PCT Pub. Date: May 31, 2019

(65) Prior Publication Data
US 2020/0345744 A1 Nov. 5, 2020

(30) Foreign Application Priority Data

Nov. 23, 2017 (EP) .................................... 17203377

(51) Int. Cl.
*A61K 31/53* (2006.01)
*A61P 9/06* (2006.01)
(Continued)

(52) U.S. Cl.
CPC .......... *A61K 31/53* (2013.01); *A61K 31/4985* (2013.01); *A61K 31/5025* (2013.01);
(Continued)

(58) Field of Classification Search
CPC ................................. A61K 31/53; A61P 9/06
See application file for complete search history.

(56) References Cited

U.S. PATENT DOCUMENTS 6,573,263 B2  6/2003 Niewoehner et al.
7,851,472 B2  12/2010 Schmidt et al.
(Continued)

FOREIGN PATENT DOCUMENTS

EP  1347978  10/2003
EP  1548011  6/2005
(Continued)

OTHER PUBLICATIONS

Priori et. al. (Eur. Heart J. (2015) 36:2793-2867). (Year: 2015).*
(Continued)

*Primary Examiner* — Marcos L Sznaidman
(74) *Attorney, Agent, or Firm* — Meunier Carlin & Curfman LLC

(57) ABSTRACT

The invention provides compounds which are selective PDE2 inhibitors for use in the treatment of tachycardia or tachyarrhythmia Such compounds are particularly suitable for use in the treatment of any of the following conditions: atrial tachycardia, atrial fibrillation, atrial flutter, paroxysmal supraventricular tachycardia, premature ventricular contractions (PVCs), ventricular fibrillation and ventricular tachycardia, and may be used alone or in combination therapy with other conventional cardiovascular drugs, e.g. beta-blockers. In particular, the invention provides compounds which are selective PDE2 inhibitors for use in the treatment of ventricular tachycardia in patients who are suffering from, or who are at risk of suffering from heart failure, CPVT or long QT syndrome.

21 Claims, 18 Drawing Sheets

Figure 4:
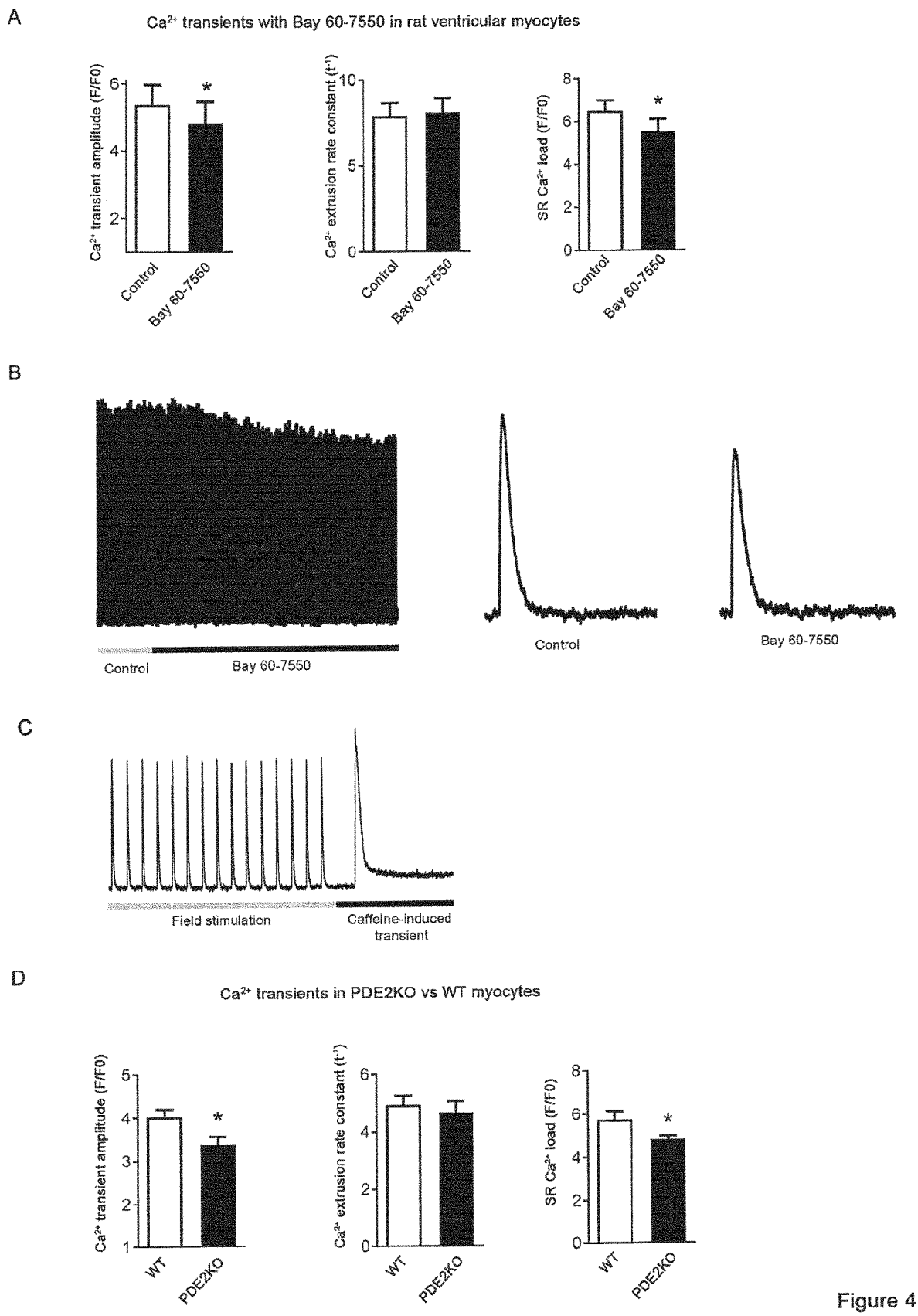

(51) Int. Cl.
```
A61K 31/4985    (2006.01)
A61K 31/5025    (2006.01)
A61K 31/52      (2006.01)
A61K 31/5517    (2006.01)
A61K 31/135     (2006.01)
```
(52) U.S. Cl.
CPC .......... *A61K 31/52* (2013.01); *A61K 31/5517* (2013.01); *A61P 9/06* (2018.01); *A61K 31/135* (2013.01)

(56) References Cited

U.S. PATENT DOCUMENTS

| | | |
|---|---|---|
| 8,598,155 B2 | 12/2013 | Helal et al. |
| 9,200,000 B2 | 12/2015 | Helal et al. |
| 9,469,637 B2 | 10/2016 | Mikami et al. |
| 9,527,841 B2 | 12/2016 | Nakamura et al. |
| 2010/0035882 A1 | 2/2010 | Ellinghaus et al. |
| 2012/0214791 A1 | 8/2012 | Helal et al. |

FOREIGN PATENT DOCUMENTS

| | | |
|---|---|---|
| EP | 1749824 | 2/2007 |
| EP | 3026051 | 6/2016 |
| WO | 2002/050078 | 6/2002 |
| WO | 2004/41258 | 5/2004 |
| WO | 2004/089953 | 10/2004 |
| WO | 2005/021037 | 3/2005 |
| WO | 2005/035505 | 4/2005 |
| WO | 2005/041957 | 5/2005 |
| WO | 2005/061497 | 7/2005 |
| WO | 2006/024640 | 3/2006 |
| WO | 2006/072612 | 7/2006 |
| WO | 2006/072615 | 7/2006 |
| WO | 2010/054253 | 5/2010 |
| WO | 2012/104293 | 8/2012 |
| WO | 2012/168817 | 12/2012 |
| WO | 2013/000924 | 1/2013 |
| WO | 2014/010732 | 1/2014 |
| WO | 2014/019979 | 2/2014 |
| WO | 2016/073424 | 5/2016 |

OTHER PUBLICATIONS

Vettel et al. (Cir. Res. (2017) 120:120-132). (Year: 2017).*
Galindo-Tovar et al. (Naunyn-Schmiedeberg's Arch. Pharmacol. (2016) 389:177-186). (Year: 2016).*
International Search report and Written Opinion issued for International Application No. PCT/EP2018/082450, dated Feb. 18, 2019.
Extended European Search Report issued for European Application No. 17203377.1, dated Jun. 8, 2018.
Al-Khatib et al., 2017 AHA/ACC/HRS Guideline for Management of Patients with Ventricular Arrhythmias and the Prevention of Sudden Cardiac Death, Guidelines from AHA, 2017, Circulation. 2018;138:e272-e391.
Aronsen, J. M., et al. "Hypokalaemia induces $Ca^{2+}$ overload and $Ca^{2+}$ waves in ventricular myocytes by reducing $Na^+$, $K^+$-ATPase α2 activity." The Journal of physiology 593.6 (2015): 1509-1521.
Baartscheer, A., C. A. Schumacher, and J. W. T. Fiolet. "Small changes of cytosolic sodium in rat ventricular myocytes measured with SBF1 in emission ratio mode." Journal of molecular and cellular cardiology 29.12 (1997): 3375-3383.
Bender, Andrew T., and Joseph A. Beavo. "Cyclic nucleotide phosphodiesterases: molecular regulation to clinical use." Pharmacological reviews 58.3 (2006): 488-520.
Boess, Frank G., et al. "Inhibition of phosphodiesterase 2 increases neuronal cGMP, synaptic plasticity and memory performance." Neuropharmacology 47.7 (2004): 1081-1092.
Buijnsters, Peter, et al. "Structure-based design of a potent, selective, and brain penetrating PDE2 inhibitor with demonstrated target engagement." ACS medicinal chemistry letters 5.9 (2014): 1049-1053.

Cheung, Joseph Y., et al. "Regulation of cardiac Na+/Ca2+ exchanger by phospholemman." Annals of the New York Academy of Sciences 1099.1 (2007): 119-134.
Despa, Sanda, Jerry B. Lingrel, and Donald M. Bers. "Na+/K+-ATPase α2-isoform preferentially modulates Ca2+ transients and sarcoplasmic reticulum Ca2+ release in cardiac myocytes." Cardiovascular research 95.4 (2012): 480-486.
Faggioni, Michela, and Björn C. Knollmann. "Arrhythmia protection in hypokalemia: a novel role of Ca2+-Activated K+ currents in the ventricle." (2015): 1371-1373.
Global Data Drug Report ND7001, Dec. 29, 2015, 4 pages.
Global Data Drug Report TAK-915, Dec. 2, 2016, 3 pages.
Gold, Matthew G., et al. "Molecular basis of AKAP specificity for PKA regulatory subunits." Molecular cell 24.3 (2006): 383-395.
Gomez, Laurent, and J. Guy Breitenbucher. "PDE2 inhibition: potential for the treatment of cognitive disorders." Bioorganic & medicinal chemistry letters 23.24 (2013): 6522-6527.
Gomez, Laurent, et al. "Design and synthesis of novel and selective phosphodiesterase 2 (PDE2a) inhibitors for the treatment of memory disorders." Journal of medicinal chemistry 60.5 (2017): 2037-2051.
Kannankeril, Prince J., et al. "Mice with the R176Q cardiac ryanodine receptor mutation exhibit catecholamine-induced ventricular tachycardia and cardiomyopathy." Proceedings of the National Academy of Sciences 103.32 (2006): 12179-12184.
Kranias, E. G., and Donald M. Bers. "Calcium and cardiomyopathies." Calcium Signalling and Disease. Springer, Dordrecht, 2007. 523-537.
Maehara, Shunsuke, et al. "Pharmacological characterization of a novel potent, selective, and orally active phosphodiesterase 2A inhibitor, PDM-631." European Journal of Pharmacology 811 (2017): 110-116.
Masood, Anbrin, et al. "Anxiolytic effects of phosphodiesterase-2 inhibitors associated with increased cGMP signaling." Journal of Pharmacology and Experimental Therapeutics 331.2 (2009): 690-699.
Mehel, Hind, et al. "Phosphodiesterase-2 is up-regulated in human failing hearts and blunts β-adrenergic responses in cardiomyocytes." Journal of the American College of Cardiology 62.17 (2013): 1596-1606.
Mikami, Satoshi, et al. "Discovery of a novel series of pyrazolo [1,5-a] pyrimidine-based phosphodiesterase 2A inhibitors structurally different from N-((1S)-1-(3-fluoro-4-(trifluoromethoxy) phenyl)-2-methoxyethyl)-7-methoxy-2-oxo-2, 3-dihydropyrido [2, 3-b] pyrazine-4 (1H)-carboxamide (TAK-915), for the treatment of cognitive disorders." Chemical and Pharmaceutical Bulletin 65.11 (2017): 1058-1077.
Mikami, Satoshi, et al. "Discovery of Clinical Candidate N-((1 S)-1-(3-Fluoro-4-(trifluoromethoxy) phenyl)-2-methoxyethyl)-7-methoxy-2-oxo-2, 3-dihydropyrido [2, 3-b] pyrazine-4 (1 H)-carboxamide (TAK-915): A Highly Potent, Selective, and Brain-Penetrating Phosphodiesterase 2A Inhibitor for the Treatment of Cognitive Disorders." Journal of medicinal chemistry 60.18 (2017): 7677-7702.
Mohler, Peter J., et al. "Ankyrin-B mutation causes type 4 long-QT cardiac arrhythmia and sudden cardiac death." Nature 421.6923 (2003): 634-639.
Osadchii, Oleg E. "Impact of hypokalemia on electromechanical window, excitation wavelength and repolarization gradients in guinea-pig and rabbit hearts." PLoS One 9.8 (2014): e105599.
Pezhouman, Arash, et al. "Molecular basis of hypokalemia-induced ventricular fibrillation." Circulation 132.16 (2015): 1528-1537.
Pogwizd, Steven M., and Donald M. Bers. "Cellular basis of triggered arrhythmias in heart failure." Trends in cardiovascular medicine 14.2 (2004): 61-66.
Priori, S. G., et al. "Spaulding Ch., Veldhuisen DJ 2015 ESC Guidelines for the management of patients with ventricular arrhythmias and the prevention of sudden cardiac death: The Task Force for the Management of Patients with Ventricular Arrhythmias and the Prevention of Sudden Cardiac Death of the European Society of Cardiology (ESC)." European heart journal 36.41 (2015): 2793-2867.
Redrobe, John P., et al. "In vitro and in vivo characterisation of Lu AF64280, a novel, brain penetrant phosphodiesterase (PDE) 2A

(56) References Cited

OTHER PUBLICATIONS inhibitor: potential relevance to cognitive deficits in schizophrenia." Psychopharmacology 231.16 (2014): 3151-3167.

Rombouts, Frederik Jr, et al. "Pyrido [4, 3-e] [1, 2, 4] triazolo [4, 3-a] pyrazines as selective, brain penetrant phosphodiesterase 2 (PDE2) inhibitors." ACS medicinal chemistry letters 6.3 (2015): 282-286.

Souness, John E., et al. "Evidence that cyclic AMP phosphodiesterase inhibitors suppress TNFα generation from human monocytes by interacting with a 'low-affinity' phosphodiesterase 4 conformer." British journal of pharmacology 118.3 (1996): 649-658.

Swift, Fredrik, et al. "The Na+/K+-ATPase α2-isoform regulates cardiac contractility in rat cardiomyocytes." Cardiovascular research 75.1 (2007): 109-117.

Thienpont, Bernard, et al. "The H3K9 dimethyltransferases EHMT1/2 protect against pathological cardiac hypertrophy." The Journal of clinical investigation 127.1 (2017): 335-348.

Trabanco, Andrés A., Peter Buijnsters, and Frederik JR Rombouts. "Towards selective phosphodiesterase 2A (PDE2A) inhibitors: a patent review (2010-present)." Expert opinion on therapeutic patents 26.8 (2016): 933-946.

Vettel, Christiane, et al. "Phosphodiesterase 2 protects against catecholamine-induced arrhythmia and preserves contractile function after myocardial infarction." Circulation research 120.1 (2017): 120-132.

Wanichawan, Pimthanya, et al. "Development of a high-affinity peptide that prevents phospholemman (PLM) inhibition of the sodium/calcium exchanger 1 (NCX1)." Biochemical Journal 473.15 (2016): 2413-2423.

Weeks, J. L., et al. "High biochemical selectivity of tadalafil, sildenafil and vardenafil for human phosphodiesterase 5A1 (PDE5) over PDE11A4 suggests the absence of PDE11A4 cross-reaction in patients." International journal of impotence research 17.1 (2005): 5-9.

Zaccolo, Manuela, and Matthew A. Movsesian. "cAMP and cGMP signaling cross-talk: role of phosphodiesterases and implications for cardiac pathophysiology." Circulation research 100.11 (2007): 1569-1578.

Zoccarato, Anna, et al. "Cardiac hypertrophy is inhibited by a local pool of cAMP Yegulated by phosphodiesterase 2." Circulation research 117.8 (2015): 707-719.

* cited by examiner

A  Experimental protocol for NKA current measurement
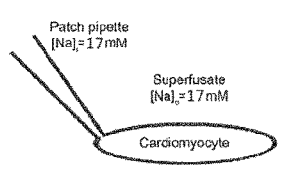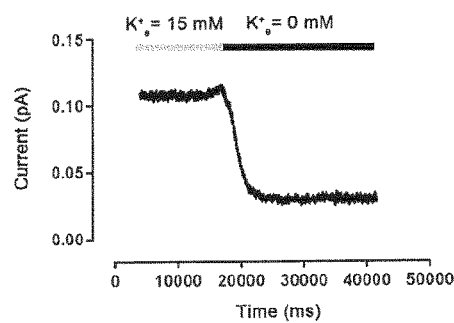
B
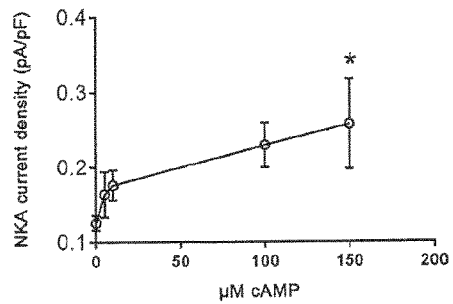
C
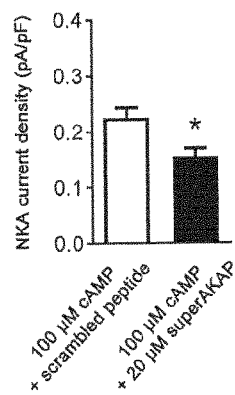
Figure 1

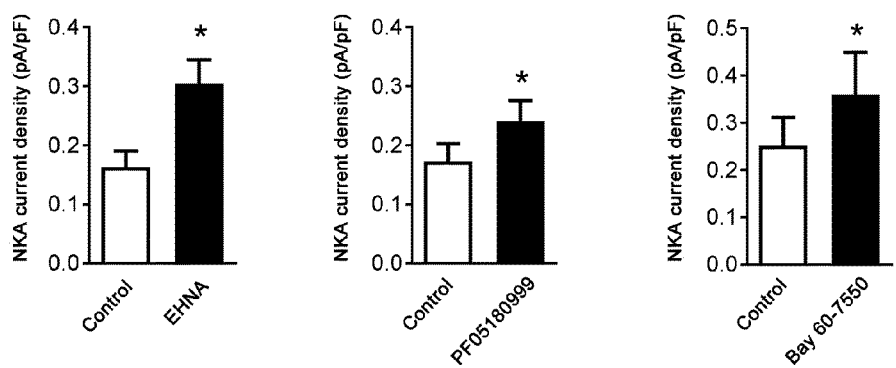
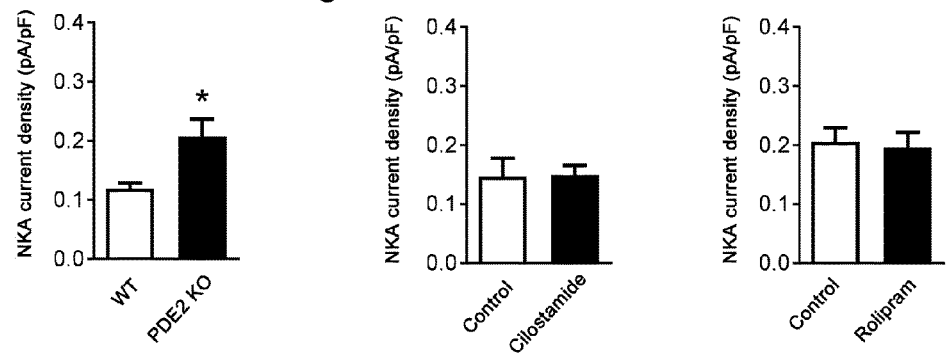
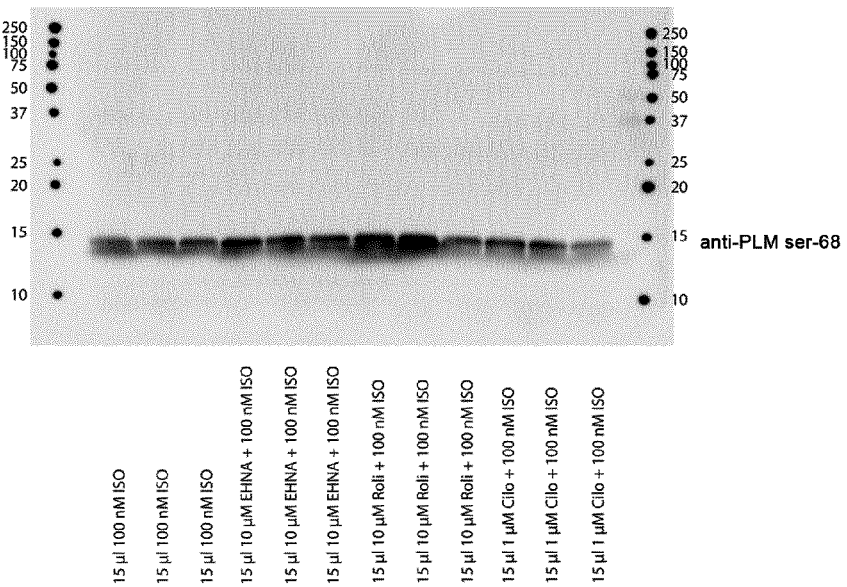
Figure 2

A
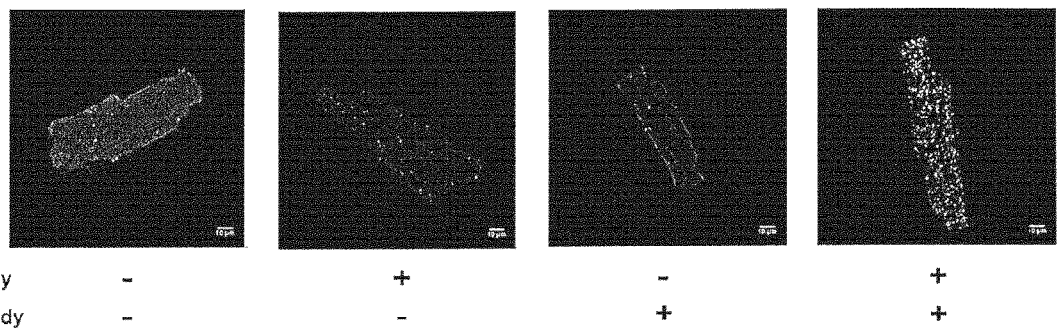
Proximity ligation assay of NKA and PDE2 in rat ventricular myocytes
| NKA antibody | − | + | − | + |
| PDE2 antibody | − | − | + | + |
B
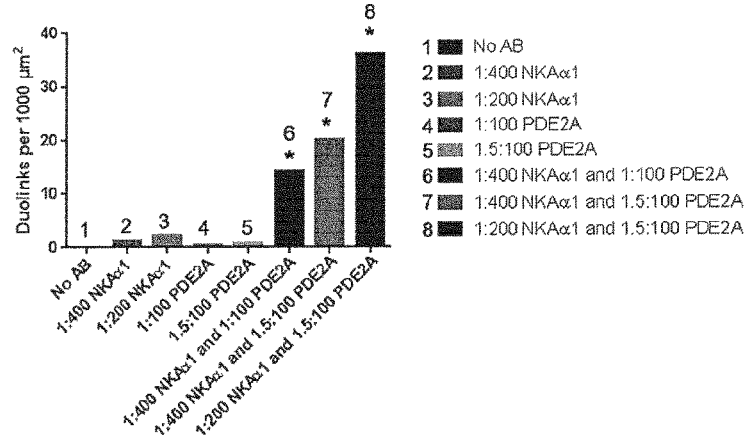
1. No AB
2. 1:400 NKAα1
3. 1:200 NKAα1
4. 1:100 PDE2A
5. 1.5:100 PDE2A
6. 1:400 NKAα1 and 1:100 PDE2A
7. 1:400 NKAα1 and 1.5:100 PDE2A
8. 1:200 NKAα1 and 1.5:100 PDE2A
C
Co-immunoprecipitations of NKA and PDE2 in HEK293 cells
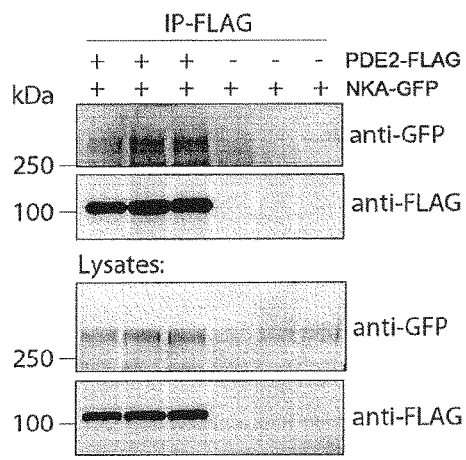
Figure 3

A

Representative tracings of measurements of the activity of Ca²⁺ handling proteins

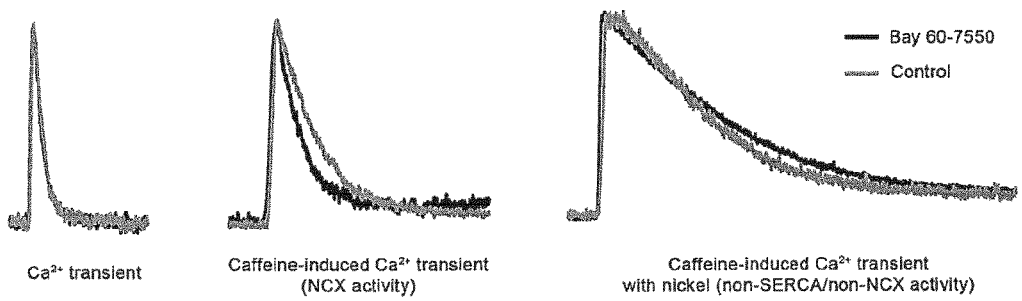

Ca²⁺ transient

Caffeine-induced Ca²⁺ transient (NCX activity)

Caffeine-induced Ca²⁺ transient with nickel (non-SERCA/non-NCX activity)

B

Ca²⁺ handling protein activity with Bay 60-7550 in rat ventricular myocytes

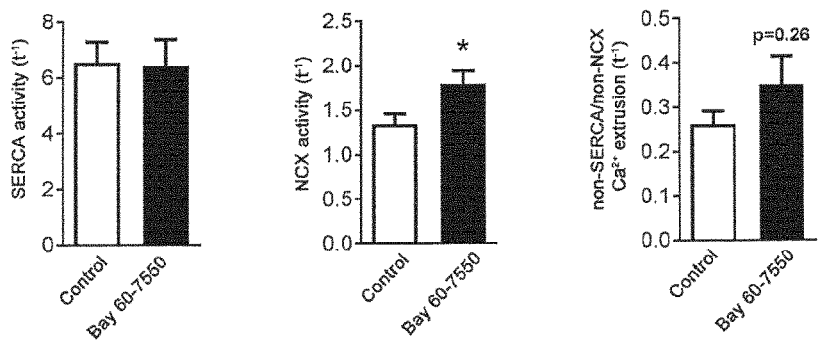

C

Ca²⁺ handling protein activity in PDE2KO vs WT myocytes

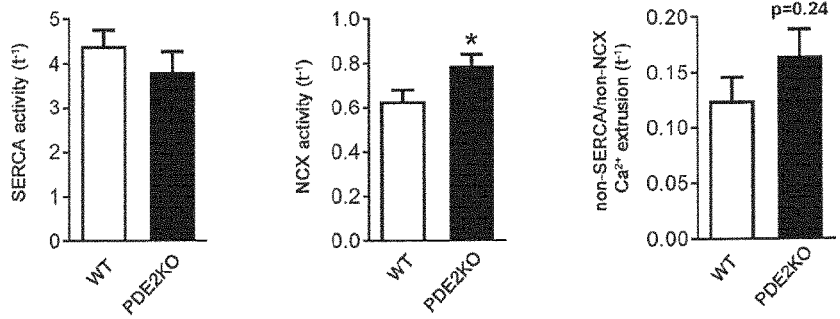

D

Intracellular Na⁺ measured with SBFI

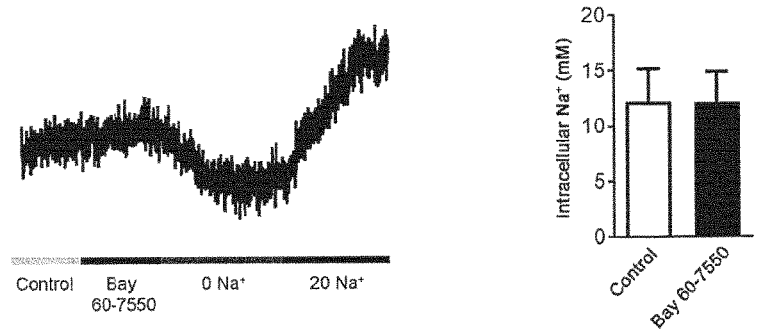

Figure 5

A
Representative tracings of L-type $Ca^{2+}$ current with Bay 60-7550 in rat ventricular myocytes
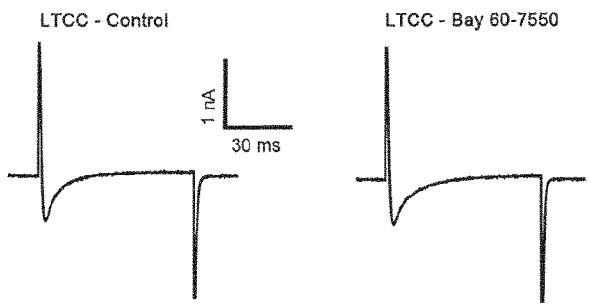
B
L-type $Ca^{2+}$ current with Bay 60-7550 in rat ventricular myocytes
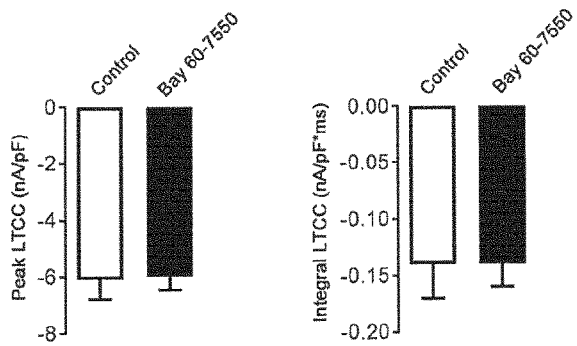
C
$Ca^{2+}$ sparks measurements with Bay 60-7550 in rat ventricular myocytes
D
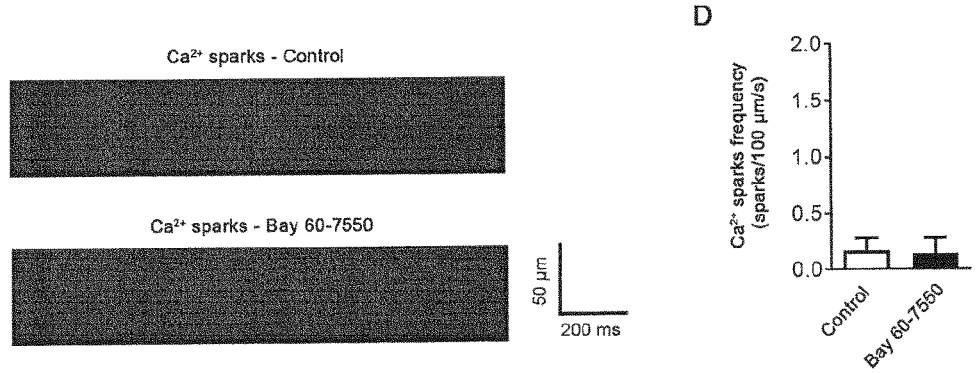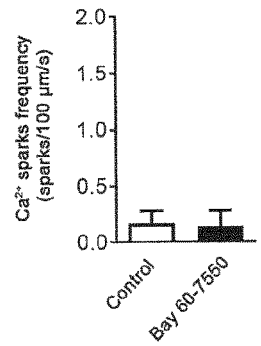
E
$Na^+$ currents with Bay 60-7550 in rat ventricular myocytes
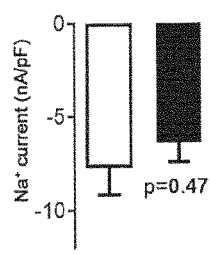
Figure 6

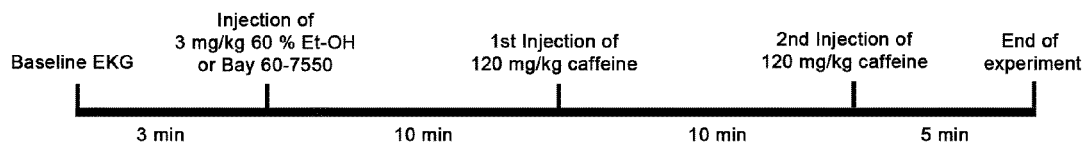
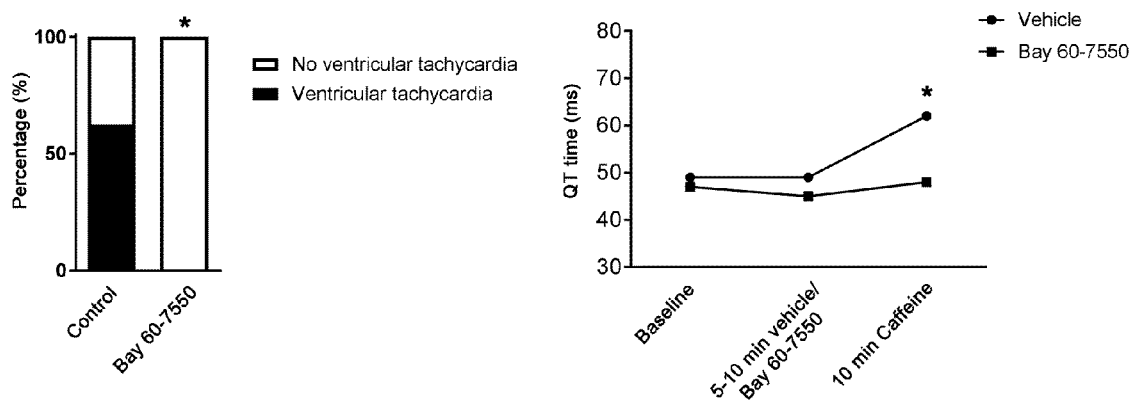
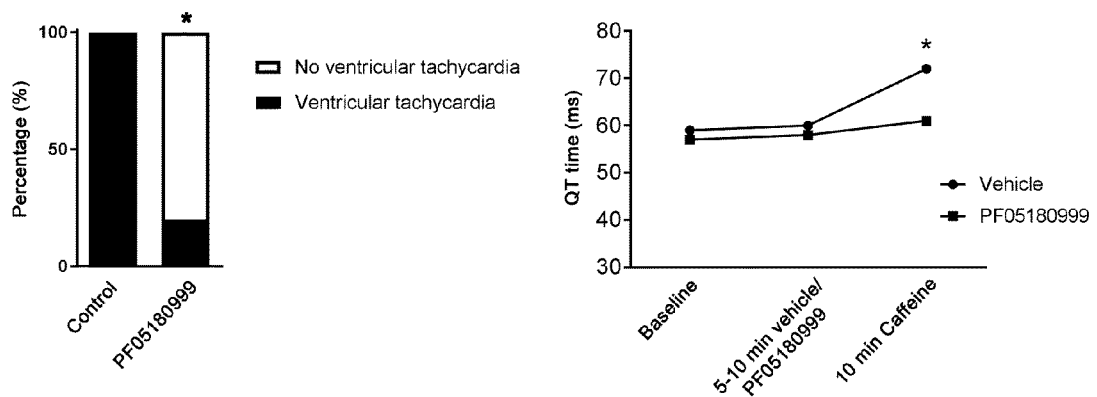
Figure 9

A
*In vivo* protocol in HF and AnkB+/- mice with superAKAP
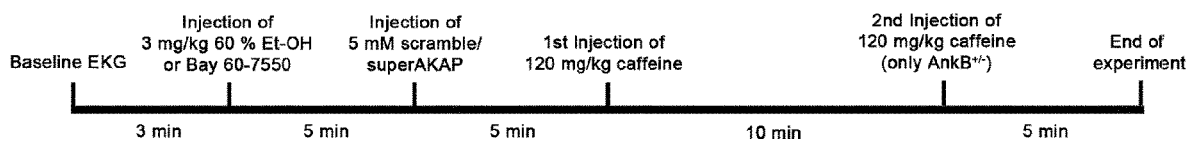
B
Ventricular arrhythmias with Bay 60-7550 and superAKAP in heart failure mice
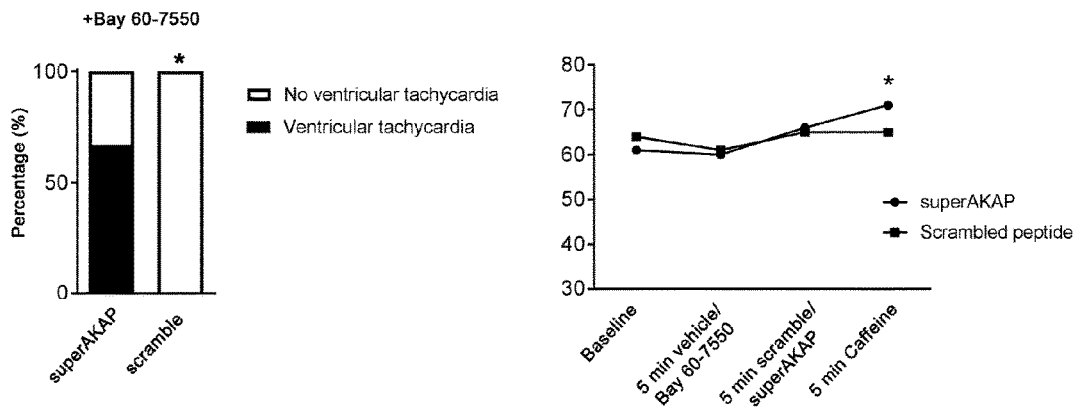
C
Ventricular arrhythmias with Bay 60-7550 and superAKAP in AnkB+/- mice
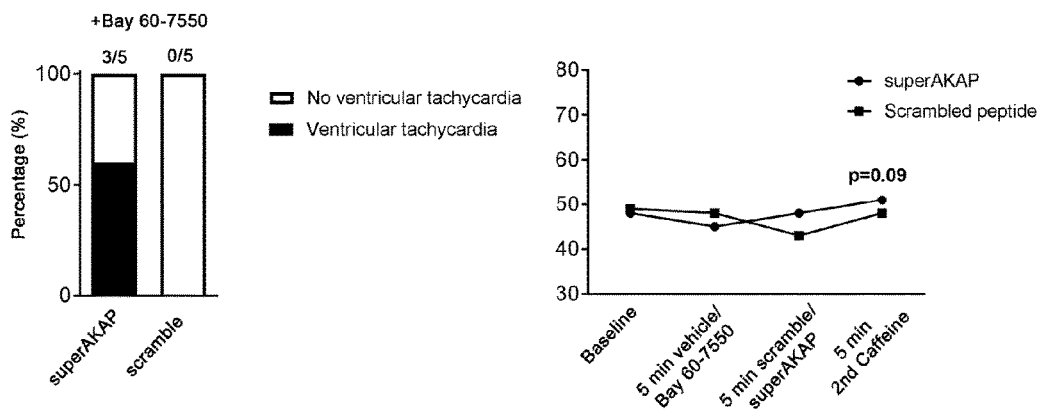
Figure 11

A
Proposed mechanism for local regulation
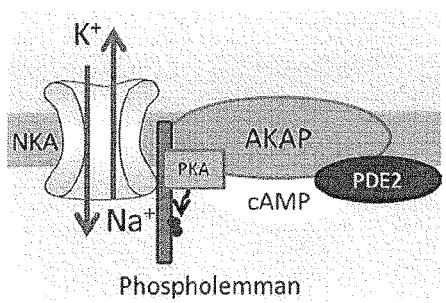
B
Proposed mechanism for disruption of local AKAP-bound PKA-RII
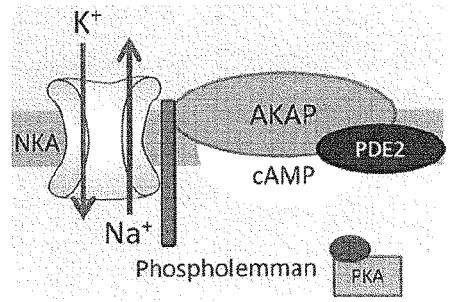
Figure 12

Cardiomyocyte-specific PDE2A-mRNA expression

A

Ventricular tachycardia with PDE2 inhibitors in HF mice

A
*In vivo* protocol in CPVT mice
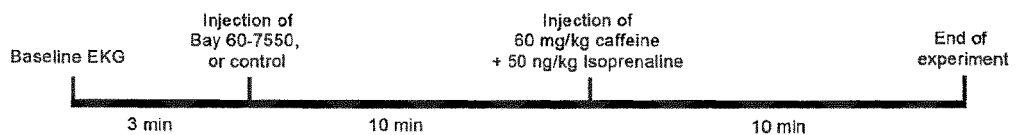
B
Ventricular tachycardia with Bay 60-7550 in CPVT mice
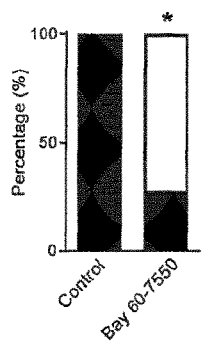
Figure 18

TREATMENT OF TACHYCARDIA

CROSS-REFERENCE TO RELATED APPLICATIONS

This application is a U.S. National stage application of International Application No. PCT/EP2018/082450, filed Nov. 23, 2018, which claims priority to and the benefit of European Application No. 17203377.1, filed Nov. 23, 2017. These above-identified applications are hereby incorporated by reference in their entireties.

FIELD OF THE INVENTION

The present invention generally relates to the treatment and/or prevention of tachycardia or tachyarrhythmia. Specifically, it relates to the use of phosphodiesterase 2 (PDE2) inhibitors in methods for the treatment and/or prevention of such conditions, in particular ventricular tachycardia.

BACKGROUND OF THE INVENTION

Cardiac arrhythmias are a group of conditions in which the heart rhythm is abnormal, either too fast or too slow. A heart rate that is too fast—typically above 100 beats per minute in an adult human—is known as "tachycardia" and one that is too slow—typically below 60 beats per minute—is known as "bradycardia". A tachycardia which is associated with an irregularity in the normal heart rhythm may be known as a "tachyarrhythmia". However, the terms "tachycardia" and "tachyarrhythmia" are often used interchangeably in the art and, for practical purposes, may be used by clinicians to describe any cardiac rhythm disorder associated with an increased heart rate. Although many arrhythmias are not serious, some may predispose the subject to complications such as heart failure, stroke, or cardiac arrest.

Arrhythmias arise due to abnormal impulse formation (increased automaticity and triggered activity), abnormal impulse conduction (re-entry mechanisms) and problems associated with the electrical conduction system of the heart. Arrhythmias may be categorized along two axis: slow vs fast (bradycardias vs tachycardias) and atrial vs ventricular.

Supraventricular tachycardias include atrial tachycardia, atrial fibrillation, atrial flutter and paroxysmal supraventricular tachycardia. Ventricular tachyarrhythmias include premature ventricular contractions (PVCs), ventricular fibrillation and ventricular tachycardia. Ventricular tachycardia is a type of often regular and fast heart rate that arises from improper electrical activity in the ventricles of the heart. It may occur during or after myocardial infarction, in a failing or hypertrophied heart, in cardiomyopathies, or in a structurally normal heart, and can result in cardiac arrest.

Most arrhythmias, including tachycardia, can be effectively treated using medications, medical procedures such as a pacemaker, or by surgery (e.g. ablation). Current pharmacological treatment strategies for ventricular tachyarrhythmias, for example, include agents blocking the beta-adrenergic receptor and blockers of $Ca^{2+}$, $Na^+$ and $K^+$ channels. However, these agents often prove ineffective for patients having ventricular tachyarrhythmias despite optimal treatment. Optimal dosing of beta-blockers is often limited by side-effects (e.g. bradycardia, hypotension, fatigue, etc.), while $Ca^{2+}$ blockers are not commonly used during heart failure due to negative effects on contractility. Especially $Na^+$ blockers, but also some $K^+$ blockers, are contraindicated in patients with structural heart disease due to its pro-arrhythmic effects (Priori, S. G., et al., 2015 *ESC Guidelines for the management of patients with ventricular arrhythmias and the prevention of sudden cardiac death: The Task Force for the Management of Patients with Ventricular Arrhythmias and the Prevention of Sudden Cardiac Death of the European Society of Cardiology (ESC). Endorsed by: Association for European Paediatric and Congenital Cardiology (AEPC).* Eur Heart J, 2015. 36(41): 2793-867; and Al-Khatib et al., Guidelines from AHA, 2017).

Beta-blockers, such as Metoprolol, are the standard treatment for most types of tachyarrhythmias, including ventricular tachycardias. Other drugs in use for the treatment of serious (possibly fatal) abnormal heart rhythm (such as ventricular tachycardia, paroxysmal supraventricular tachycardia and atrial fibrillation) include propafenone hydrochloride (Rythmol). It is used to restore normal heart rhythm and maintain a regular, steady heartbeat. Propafenone is a Class 1C anti-arrhythmic drug with local anaesthetic effects and a direct stabilising action on myocardial membranes. Adverse side-effects associated with Rythmol occur most frequently in the gastrointestinal, cardiovascular and central nervous systems. In about 20% of patients treatment with Rythmol must be discontinued due to adverse reactions.

There thus remains a need for new drugs for the treatment or prevention of tachycardias, in particular ventricular tachycardias. We propose herein the local and selective activation of $Na^+/K^+$-ATPase (sodium potassium adenosine triphosphatase or "NKA", also known as the $Na^+/K^+$ pump or sodium-potassium pump) by the inhibition of PDE2 as a new treatment strategy for such disorders. This mechanism differs from the mechanism of conventional drugs, such as beta-blockers and Class 1 anti-arrhythmics, which are used to treat ventricular tachycardias by targeting beta-adrenergic receptors, calcium channels, $Na^+$ channels or $K^+$ channels.

PDE2 is one of a number of different phosphodiesterases (PDEs) found in mammals. The PDE family of enzymes regulates intracellular levels of the secondary messenger cyclic nucleotides cAMP and/or cGMP through hydrolytic control. These cyclic nucleotides function as intracellular signaling molecules in all mammalian cells. PDE enzymes hydrolyse cAMP and/or cGMP by breaking the phosphodiester bonds to form the corresponding monophosphates.

The different PDEs are sub-divided into 11 families (PDE1 to PDE11) based on substrate specificity, inhibitor sensitivity and, more recently, based on sequence homology. The 11 families are coded by 21 genes providing several families with multiple members. PDEs in the same family are functionally related. PDEs have different substrate specificities—some are cAMP selective hydrolases (PDE4, PDE7 and PDE8), whereas others are cGMP selective hydrolases (PDE5, PDE6 and PDE9). The others, including PDE2, are dual-substrate PDEs responsible for hydrolysis of both cAMP and cGMP.

Several PDE inhibitors, in particular PDE3, PDE4 and PDE5 inhibitors, are approved for clinical use. PDE3 inhibitors, such as Milrinone, are used in cardiovascular therapies. PDE2 shows the highest expression in the brain, but is also found in other tissues. Inhibition of PDE2 results in increased cAMP and cGMP levels that may improve cognitive function. To date, PDE2 inhibitors have mainly been documented in the literature for use in the treatment of various cognitive disorders, e.g. in neuronal development, learning and memory, in the treatment of neurological disorders, and neurodegenerative disorders such as dementia, Alzheimer's disease, etc. Several PDE2 inhibitors have undergone phase I clinical trials for cognitive disorders, including TAK-915 (Takeda), ND-7001 (Neuro3d/Evotec), and PF-05180999 (Pfizer). For example, in Mikami et al., *J.*

*Med. Chem.*, 2017, 60(18): 7677-7702, oral administration of TAK-915 is shown to elevate 3′,5′-cyclic guanosine monophosphate (cGMP) levels in mouse brains and to improve cognitive performance in rats. As a result of these studies, the compound was advanced into human clinical trials.

Other documents which describe PDE2 inhibitors include EP 3026051, WO 2005/021037 and WO 2012/168817. In EP 3026051 it is suggested that the compounds have a PDE2A inhibitory activity and are useful as a prophylactic or therapeutic drug for schizophrenia, Alzheimer's disease and the like. In WO 2005/021037, known PDE2 inhibitors are combined with known pulmonary surfactants for use in the treatment of pulmonary lesions, specifically ARDS (Adult Respiratory Distress Syndrome), IRDS (Infant Respiratory Distress Syndrome), ALI (Acute Lung Injury) and Asthma bronchiale. In WO 2012/168817 various compounds are described for use as PDE2 inhibitors and/or CYP3A4 inhibitors and are proposed for use in treating central nervous system disorders, cognitive disorders, schizophrenia, and dementia. None of these documents propose the use of any PDE2 inhibitor in the treatment of any cardiac-related disorder.

PDE2 is also expressed in heart tissue and there has been some speculation, albeit unsupported, relating to the use of PDE2 inhibitors in the treatment or prevention of cardiac arrhythmias (see e.g. WO 2006/072612, WO 2004/089953, WO 2016/073424 and WO 2006/024640). WO 2004/089953 and WO 2006/024640, for example, relate to new PDE2 inhibitors which, it is postulated, may be effective in the treatment or prevention of an extremely wide range of conditions, including pneumonia, arthritis, retinal blindness, Alzheimer's disease, etc. On the basis that PDE2 is shown in myocardium, these documents propose that the compounds may have the potential to protect against "cardiac arrhythmias", but no evidence is provided to support this. There is also nothing to suggest whether the compounds which are disclosed in these documents may be suitable for the treatment or prevention of any particular group of cardiac arrhythmias, let alone ventricular tachycardias. Against this background, it could not have been predicted that the PDE2 inhibitors would necessarily be suitable for the treatment of tachycardia as evidenced herein.

The term "cardiac arrhythmia" broadly defines a range of different cardiac rhythm disorders that require different therapeutic approaches. Both the origin (atrial vs ventricular) and type (tachyarrhythmia vs bradyarrhythmia) of arrhythmia are important to decide before initiating a therapy. Atrial arrhythmias are often treated in a completely different manner than ventricular arrhythmias. For example, adenosine and cardiac glycosides (e.g. digoxin) are used to treat various atrial arrhythmias, but could induce or exacerbate ventricular arrhythmias. Similarly, a treatment that is suitable for a tachyarrhythmia is generally contraindicated in the case of bradyarrhythmia. For example, beta-blockers such as Metoprolol are a treatment for tachyarrhythmia, but cause bradyarrhythmias. Beta-blockers (e.g. Metoprolol) are therefore contraindicated in all types of bradyarrhythmias. Treatment of arrhythmias can also depend on the underlying cause or condition. Treatment of ventricular tachyarrhythmias in heart failure or following a myocardial infarction is different from treatment of ventricular tachyarrhythmias in genetic diseases such as CPVT and long QT syndrome. For example, Flecainide (a $Na^+$ channel blocker which is a Class 1 anti-arrhythmic drug) is commonly used in CPVT and long QT syndrome, but is contraindicated in heart failure and following a myocardial infarction. Thus, depending on the origin and type, cardiac arrhythmias can be divided into different groups which require a different therapeutic approach. A general reference to the treatment of "cardiac arrhythmia" is not sufficient to suggest which type of arrhythmia might be treated.

In contrast to the prior art, the present invention relates to the treatment or prevention of tachycardias and, in particular, ventricular tachycardia. Others positively teach away from the findings presented herein. For example, Vettel, C., et al. (*Phosphodiesterase 2 Protects Against Catecholamine-Induced Arrhythmia and Preserves Contractile Function After Myocardial Infarction*. Circ Res, 2017. 120(1): 120-132) suggest that a greater PDE2 abundance protects against arrhythmias and improves contraction force after severe ischemic insult. They therefore propose activation of PDE2 as a therapeutic strategy to protect the heart from arrhythmia and contractile dysfunction. WO 2005/035505 further warns that PDE inhibitors may increase heart rate and even cause arrhythmia. This is contrary to our findings presented herein which support the use of PDE2 inhibitors in the treatment of tachycardia.

Lowered activity of NKA has been identified as an important upstream contributor to several arrhythmias (Faggioni, M. and B. C. Knollmann, *Arrhythmia Protection in Hypokalemia: A Novel Role of Ca2+-Activated K+ Currents in the Ventricle*. Circulation, 2015. 132(15): 1371-3), but to our knowledge no specific activators of NKA exist. The findings presented herein show that PDE2 inhibition strongly activates NKA and prevents ventricular tachyarrhythmias in mice with heart failure and inherited arrhythmia syndromes (Ankyrin$^{+/-}$ mice, a type of long QT syndrome, and Catecholaminergic Polymorphic Ventricular Tachycardia (CPVT) mice). The ability of PDE2 inhibition to prevent arrhythmias was blunted with the addition of superAKAP, a peptide that with high specificity displaces the RII-PKA from AKAPs. Together with data showing that superAKAP abrogates the effect of PDE2 inhibition on the NKA current, this suggests that PDE2 regulates NKA and prevents ventricular tachyarrhythmias by regulating cAMP levels in a local domain.

PDE2 inhibition as an anti-arrhythmic treatment as herein described represents a novel treatment strategy in two ways: 1) as an activator of NKA; and 2) by targeting cAMP levels in discrete domains. The data presented in the accompanying examples also suggests that PDE2 is up-regulated in human hypertrophy and ageing, as we found increased expression of PDE2-mRNA in cardiomyocyte-specific nuclei. This is in line with previous data (Mehel, H., et al., *Phosphodiesterase-2 is up-regulated in human failing hearts and blunts beta-adrenergic responses in cardiomyocytes*. J Am Coll Cardiol, 2013. 62(17): 1596-606) and indicates that PDE2 inhibition might be a desirable anti-arrhythmic target in human chronic heart disease.

We report herein a novel treatment strategy, namely PDE2 inhibition, for the treatment and/or prevention of tachycardia, in particular ventricular tachycardia. In particular, we have found a novel regulatory mechanism of NKA in which PDE2 locally regulates NKA activity through interaction with NKA and PKA-RII. Although not wishing to be bound by theory, we suggest that this mechanism underlies the anti-arrhythmic effects seen both in vivo and in isolated ventricular myocytes in heart failure, Ankyrin B$^{+/-}$ mice, and in CPVT. This is supported by the finding that PDE2 inhibition reduces intracellular $Ca^{2+}$ loading mainly through increased $Ca^{2+}$ extrusion through NCX (a downstream effect of increasing NKA activity) and because the anti-arrhythmic effect in vivo is abolished with superAKAP, which disrupts local AKAP-bound PKA-RII.

SUMMARY OF THE INVENTION

The invention provides a selective PDE2 inhibitor for use in the treatment of tachycardia or tachyarrhythmia, in a subject.

The invention further provides a method of treatment of tachycardia or tachyarrhythmia, in a subject in need of such treatment, said method comprising the step of administering to said subject a therapeutically effective amount of a selective PDE2 inhibitor.

The invention further provides the use of a selective PDE2 inhibitor in the manufacture of a medicament for use in the treatment of tachycardia or tachyarrhythmia, in a subject.

The invention also provides a package comprising: (i) a selective PDE2 inhibitor or a pharmaceutical composition comprising a selective PDE2 inhibitor; and (ii) printed instructions and/or a label relating to the use of (i) in the treatment of tachycardia or tachyarrhythmia, in a subject.

The invention further provides a method of combination therapy for the treatment of tachycardia or tachyarrhythmia, in a subject in need of such treatment, said method comprising the step of administering to said subject a therapeutically effective amount of a selective PDE2 inhibitor, and simultaneously or separately (e.g. sequentially) one or more cardiovascular drugs, e.g. anti-arrhythmic drugs.

The invention also provides a pharmaceutical composition comprising a selective PDE2 inhibitor and one or more cardiovascular drugs, e.g. anti-arrhythmic drugs, optionally in combination with at least one pharmaceutically acceptable carrier or excipient.

DETAILED DESCRIPTION OF THE INVENTION

The invention provides a selective PDE2 inhibitor for use in the treatment of tachycardia or tachyarrhythmia in a subject. As defined herein, "treatment" also includes prophylactic treatment, i.e. prevention.

As used herein, the term "tachycardia" refers to an elevated heart rate, i.e. a heart rate that is too fast. Typically, this may refer to a heart rate that is above 100 beats per minute in an adult human. The term "tachyarrhythmia" refers to a tachycardia which is associated with an irregularity in the normal heart rhythm (i.e. an abnormal heart rhythm). In some cases, these terms may be used interchangeably in the art to describe any cardiac rhythm disorder associated with an increased heart rate.

The invention relates, in particular, to the treatment and/or prevention of ventricular tachycardia, e.g. treatment to prevent ventricular tachycardia. As used herein, the term "ventricular tachycardia" refers to an abnormal and very fast heart rhythm that begins in the ventricles of the heart and which is caused by a malfunction in the heart's electrical system. More specifically, it refers to a pulse of more than 100 beats per minute with at least three consecutive abnormal heartbeats in a row originating from the ventricles.

In an embodiment, the invention relates to the treatment or prevention of ventricular tachycardia with reduced side-effects. Reduced side-effects include, but are not limited to, a reduction in one or more of the following adverse events: fatigue, dizziness, reduced exercise tolerance, bradycardia, nausea, diarrhea, worsening of heart failure, headache, pulmonary toxicity (interstitial pneumonitis, acute respiratory distress syndrome, diffuse alveolar hemorrhage), thyroid dysfunction, hepatotoxicity, ocular changes, and QT prolongation.

The compounds for use in the invention are selective inhibitors of PDE2, preferably selective inhibitors of human PDE2, as herein defined. An "inhibitor of PDE2" is any compound having an effect to block the degradative action of phosphodiesterase 2 (PDE2). An "inhibitor of human PDE2" should be construed accordingly. In one embodiment, the compounds for use in the invention are selective inhibitors of PDE2A, e.g. selective inhibitors of human PDE2A.

As used herein, the term "selective PDE 2 inhibitor" refers to a compound which selectively inhibits PDE2 over other PDE types, i.e. which inhibits PDE2 more strongly than other PDE types and particularly one or more of the following: PDE1, PDE3, PDE4, PDE5 and PDE10. In particular, the compound may inhibit PDE2 more strongly than it inhibits PDE10. More particularly, the compound may inhibit PDE2 more strongly than it inhibits all other PDE types.

Compounds which are preferred for use in the invention are those which are a selective human PDE2 inhibitor, i.e. which selectively inhibit human PDE2 over other human PDE types, e.g. compounds which inhibit human PDE2 more strongly than one or more of the following: human PDE1, human PDE3, human PDE4, human PDE5 and human PDE10. In particular, the compound may inhibit human PDE2 more strongly than it inhibits human PDE10. More particularly, the compound may inhibit human PDE2 more strongly than it inhibits all other human PDE types.

A PDE2 inhibitor for use in the invention may have a selectivity for inhibiting the activity of PDE2 (e.g. human PDE2) which is at least 10-fold compared to at least one other PDE type (e.g. human PDE type), preferably compared to PDE10 (e.g. human PDE10), e.g. compared to all other PDE types (e.g. all other human PDE types). In some embodiments, the degree of selectivity (e.g. compared to all other PDE types or all other human PDE types) will be at least 20-fold, e.g. at least 30-fold, or at least 50-fold. In other embodiments, the degree of selectivity (e.g. compared to all other PDE types or all other human PDE types) may be at least 100-fold, at least 200-fold, at least 300-fold, at least 400-fold, at least 500-fold, or at least 1000-fold.

Inhibitors of the activity of PDE2 for use in the invention will typically inhibit PDE2, e.g. human PDE2, with an $IC_{50}$ value (the concentration which produces 50% inhibition of substrate hydrolysis) of less than about 100 nM, preferably less than about 50 nM, e.g. less than about 40 nM, less than about 30 nM, less than about 20 nM or less than about 10 nM. In some embodiments, the compounds may inhibit PDE2, e.g. human PDE2, with an $IC_{50}$ value of less than 5 nM, or less than 1 nM. Methods for the measurement of PDE activity and for the determination of $IC_{50}$ values are well known and described in the art, for example, in Weeks et al., Int. J. Impot. Res. 17:5-9, 2005, and Souness et al., British Journal of Pharmacology 118: 649-658, 1996, the entire contents of which are incorporated herein by reference.

A wide range of PDE2 inhibitors are known and described in the literature and in earlier patent publications, together with methods for their manufacture. Any compound having the desired PDE2 inhibitory activity may be used in the invention and such compounds may readily be determined, for example using PDE inhibition and selectivity assays well known in the art, such as those described in any of the following publications, the entire contents of which are incorporated herein by reference: Boess et al. (Neuropharmacology 47:1081-1092, 2004); Maehara et al. (European Journal of Pharmacology 811: 110-116, 2017); Gomez et al. (J. Med. Chem. 60: 2037-2051, 2017); and Rombouts et al. (ACS Med. Chem. Lett. 6: 282-286, 2015).

Examples of PDE2 inhibitors suitable for use in the invention include those described in any of the following documents, the entire contents of which are incorporated herein by reference: Trabanco et al., *Towards selective phosphodiesterase 2A (PDE2A) inhibitors: a patent review (2010-present)*, Expert Opinion on Therapeutic Patents, 26(8): 933-946, 2016; WO 2002/050078 (Bayer); WO 2004/089953 (Altana Pharma AG); WO 2006/024640 (Altana Pharma AG); WO 2006/072612 (Altana Pharma AG); WO 2006/072615 (Altana Pharma AG); WO 2004/41258 (Neuro3d); EP 1548011 (Neuro3d); EP 1749824 (Neuro3d); WO 2005/041957 (Pfizer Products Inc.); WO 2005/061497 (Pfizer Products Inc.); WO 2010/054253 (Biotie Therapies GmbH and Wyeth); WO 2012/104293 (Boehringer Ingelheim International GmbH); WO 2014/019979 (Boehringer Ingelheim International GmbH); WO 2013/000924 (Janssen Pharmaceutica NV); US 2012/0214791 (Pfizer); WO 2012/168817 (Pfizer); WO 2014/010732 (Takeda); EP 3 026 051 (Takeda); WO 2005/021037 (Pfizer); Mikami et al., J. Med. Chem. 60: 7677-7702, 2017; Mikami et al., Chem. Pharm. Bull. 65(11): 1058-1077, 2017; Masood et al., JPET 331(2): 690-699, 2009; Gomez et al., Bioorg. Med. Chem. Lett. 23: 6522-6527, 2013; Maehara et al., European Journal of Pharmacology 811: 110-116, 2017; Gomez et al., J. Med. Chem. 60: 2037-2051, 2017; Rombouts et al., ACS Med. Chem. Lett. 6: 282-286, 2015; Redrobe et al., Psychopharmacology 231: 3151-3167, 2014; and Buijnsters et al., ACS Med. Chem. Lett. 5:1049-1053, 2014. Pharmaceutically acceptable salts, or prodrugs of any such compounds may also be used.

Specific examples of selective PDE2 inhibitors for use in the invention include the following compounds, their pharmaceutically acceptable salts and prodrugs:

| Compound | Name | PDE2A $IC_{50}$ or Ki values * | Selectivity Data * |
|---|---|---|---|
| [structure] | BAY 60-7550 2-(3,4-dimethoxybenzyl)-7-[(2R,3R)-2-hydroxy-6-phenylhexan-3-yl]-5-methylimidazo[5,1-f][1,2,4]triazin-4(3H)-one | $IC_{50}$ = 4.7 nM (Trabanco et al., Expert Opinion on Therapeutic Patents, 26(8): 933-946, 2016) | >50 fold selectivity vs other PDEs |
| [structure] | | $IC_{50}$ = 6 nM (Trabanco et al., Expert Opinion on Therapeutic Patents, 26(8): 933-946, 2016) | |
| [structure] | | $IC_{50}$ = 3.3 nM (Trabanco et al., Expert Opinion on Therapeutic Patents, 26(8): 933-946, 2016) | |

-continued

| Compound | Name | PDE2A IC$_{50}$ or Ki values * | Selectivity Data * |
|---|---|---|---|
| | | IC$_{50}$ = 7.12 nM (Trabanco et al., Expert Opinion on Therapeutic Patents, 26(8): 933-946, 2016) | PDE10 IC$_{50}$ = 282 nM |
| | | IC$_{50}$ = 4.12 nM (Trabanco et al., Expert Opinion on Therapeutic Patents, 26(8): 933-946, 2016) | PDE10 IC$_{50}$ > 500 nM |
| | | IC$_{50}$ = 3 nM (Trabanco et al., Expert Opinion on Therapeutic Patents, 26(8): 933-946, 2016) | PDE10 IC$_{50}$ > 1000 nM |
| | | IC$_{50}$ = 5 nM (Trabanco et al., Expert Opinion on Therapeutic Patents, 26(8): 933-946, 2016) | PDE10 IC$_{50}$ = 1488 nM |
| | | IC$_{50}$ = 12 nM (Trabanco et al., Expert Opinion on Therapeutic Patents, 26(8): 933-946, 2016) | PDE10 IC$_{50}$ = 2403 nM |
| | | IC$_{50}$ = 8 nM (Trabanco et al., Expert Opinion on Therapeutic Patents, 26(8): 933-946, 2016) | PDE10 IC$_{50}$ = 1622 nM |

| Compound | Name | PDE2A IC$_{50}$ or Ki values * | Selectivity Data * |
|---|---|---|---|
| 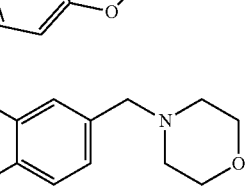 | | IC$_{50}$ = 10 nM (Buijnsters et al., ACS Med. Chem. Lett. 5: 1049-1053, 2014) | rPDE10 IC$_{50}$ = 4183 nM >210-fold selectivity vs all PDEs |
| 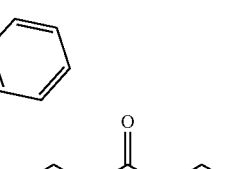 | | IC$_{50}$ = 0.29 nM (calculated from pIC$_{50}$ values in Trabanco et al., Expert Opinion on Therapeutic Patents, 26(8): 933-946, 2016) | PDE10 IC$_{50}$ = 21 nM |
| 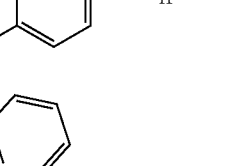 | | IC$_{50}$ = 15 nM (Trabanco et al., Expert Opinion on Therapeutic Patents, 26(8): 933-946, 2016) | |
| 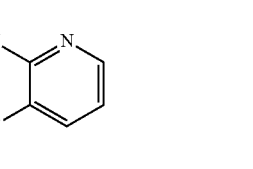 | Lu AF64280 | Ki = 20 nM (Redrobe et al., Psychopharmacology 231: 3151-3167, 2014) | PDE10 Ki = 1800 nM |
| 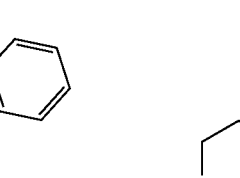 | PF-05180999 | IC$_{50}$ = 1.61 nM (U.S. 2012/ 0214791; Gomez et al., J. Med. Chem. 60: 2037-2051, 2017) | PDE selectivity: 2000x vs PDE10A |

-continued

| Compound | Name | PDE2A IC$_{50}$ or Ki values * | Selectivity Data * |
|---|---|---|---|
| | | IC$_{50}$ = 2.30 nM (Trabanco et al., Expert Opinion on Therapeutic Patents, 26(8): 933-946, 2016) | >500-fold selective over other members of the PDE family |
| | TAK-915 N-((1S)-1-(3-fluoro-4-(trifluoromethoxy)phenyl)-2-methoxyethyl)-7-methoxy-2-oxo-2,3-dihydropyrido[2,3-b]pyrazine-4-(1H)-carboxamide | IC$_{50}$ = 0.61 nM (Mikami et at., J. Med. Chem. 60: 7677-7702, 2017) | PDE selectivity: 4100 x (vs PDE1A) |
| | N-(1S)-2-hydroxy-2-methyl-1-(4-(trifluoromethoxy)-phenyl)propyl)-5-(1H-pyrazol-1-yl)pyrazolo[1,5-a]pyrimidine-3-carboxamide | IC$_{50}$ = 5.4 nM (Mikami et al., Chem. Pharm. Bull. 65(11): 1058-1077, 2017) | 630-fold selectivity vs other PDEs |
| | N-(1S)-2-hydroxy-2-methyl-1-(4-(trifluoromethoxy)-phenyl)propyl)-5-(4-methyl-1H-1,2,3-triazol-1-yl)pyrazolo[1,5-a]pyrimidine-3-carboxamide | IC$_{50}$ = 5.4 nM (Mikami et al., Chem. Pharm. Bull. 65(11): 1058-1077, 2017) | 690-fold selectivity vs other PDEs |
| | N-(1S)-2-hydroxy-2-methyl-1-(4-(trifluoromethoxy)-phenyl)propyl)-5-(3-methyl-1H-1,2,4-triazol-1-yl)pyrazolo[1,5-a]pyrimidine-3-carboxamide | IC$_{50}$ = 11 nM (Mikami et al., Chem. Pharm. Bull. 65(11): 1058-1077, 2017) | 610-fold selectivity vs other PDEs |

-continued

| Compound | Name | PDE2A IC$_{50}$ or Ki values * | Selectivity Data * |
|---|---|---|---|
| | | IC$_{50}$ = 5.1 nM (Mikami et al., Chem. Pharm. Bull. 65(11): 1058-1077, 2017) | |
| | | IC$_{50}$ = 24 nM (Mikami et al., Chem. Pharm. Bull. 65(11): 1058-1077, 2017) | |
| | ND-7001 3-(8-methoxy-1-methyl-2-oxo-7-phenyl-2,3-dihydro-1H-benzo[e]-[1,4]diazepin-5-yl) benzamide | Ki = 114 nM (Masood et al., JPET 331(2): 690-699, 2009) | |
| | PDM-631 ((S)-3-cyclopropyl-6-methyl-1-(1-(4-(trifluoromethoxy) phenyl)propan-2-yl)-1,5-dihydro-4H-pyrazolo[3,4-d]pyrimidin-4-one | IC$_{50}$ = 1.5 nM (Maehara et al., European Journal of Pharmacology 811: 110-116, 2017) | >2000-fold selectivity vs other PDEs (less than 10% inhibition at 1 μM) |
| | DNS-8254 (5S)-1-[(3-bromo-4-fluorophenyl) carbonyl]-3,3-difluoro-5-{5-methyl-[1,2,4]triazolo[1,5-a]pyrimidin-7-yl} piperidine | IC$_{50}$ = 8 nM (Gomez et al., J. Med. Chem. 60: 2037-2051, 2017) | PDE10A IC$_{50}$ = 1700 nM |

| Compound | Name | PDE2A IC$_{50}$ or Ki values * | Selectivity Data * |
|---|---|---|---|
| | 1-[2,3-dihydro-1-benzofuran-5-yl)carbonyl]-3-{5-methyl-[1,2,4]-triazolo[1,5-a]pyrimidin-7-yl}piperidine | IC$_{50}$ = 3 nM (Gomez et al., J. Med. Chem. 60: 2037-2051, 2017) | |
| | 6-[(3-{5-methyl-[1,2,4]triazolo[1,5-a]pyrimidin-7-yl}piperidin-1-yl)carbonyl]quinolone | IC$_{50}$ = 2 nM (Gomez et al., J. Med. Chem. 60: 2037-2051, 2017) | |
| | | IC$_{50}$ = 4.2 nM (U.S. Pat. 7,851,472) | |
| | | hPDE2A IC$_{50}$ = 29 nM (Rombouts et al., ACS Med. Chem. Lett. 6: 282-286, 2015) | rPDE10 IC$_{50}$ = 480 nM |
| | | hPDE2A IC$_{50}$ = 3 nM (Rombouts et al., ACS Med. Chem. Lett. 6: 282-286, 2015) | rPDE10 IC$_{50}$ = 2450 nM |

| Compound | Name | PDE2A IC$_{50}$ or Ki values * | Selectivity Data * |
|---|---|---|---|
| 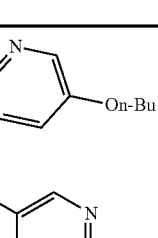 | | hPDE2A IC$_{50}$ = 54 nM (Rombouts et al., ACS Med. Chem. Lett. 6: 282-286, 2015) | rPDE10 IC$_{50}$ = 3800 nM |
| (structure with NH$_2$, purine, and hydroxynonyl chain) | EHNA (erythro-9-(2-hydroxy-3-nonyl)adenine) | | |

* values taken from the listed publications

Preferred for use in the invention are the following selective PDE2 inhibitors: TAK-915, ND-7001, PF-05180999, Lu AF64280, and their pharmaceutically acceptable salts or prodrugs. Particularly preferred for use in the invention are PF-05180999, TAK-915, their pharmaceutically acceptable salts and prodrugs thereof.

The PDE inhibitory activity of such compounds may be tested by methods known in the art, including those described in any of the following, the entire contents of which are incorporated herein by reference: Boess et al., Neuropharmacology 47:1081-1092, 2004; Maehara et al., European Journal of Pharmacology 811: 110-116, 2017; Gomez et al., J. Med. Chem. 60: 2037-2051, 2017; Rombouts et al., ACS Med. Chem. Lett. 6: 282-286, 2015; and Redrobe et al., Psychopharmacology 231: 3151-3167, 2014. Determination of the specificity of a compound to various PDEs may involve an assay to isolate specific PDE families, to measure PDE activity in terms of cGMP/cAMP degradation, and to test the extent to which the compound in question inhibits the activity.

Any of the PDE2 inhibitor compounds herein described may be used in the form of a pharmaceutically acceptable salt. The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilises the charge on the parent compound.

If the PDE2 inhibitor compound for use in the invention is a base, a suitable pharmaceutically acceptable salt may be prepared by reaction of the free base with an organic or inorganic acid. Non-limiting examples of acids which may be used for this purpose include hydrochloric acid, hydrobromic acid, sulfuric acid, sulfonic acid, methanesulfonic acid, phosphoric acid, fumaric acid, succinic acid, lactic acid, citric acid, tartaric acid, maleic acid, acetic acid, trifluoroacetic acid and ascorbic acid. If the PDE2 inhibitor compound for use in the invention is an acid, a suitable pharmaceutically acceptable salt may be prepared by reaction of the free acid with an organic or inorganic base. Non-limiting examples of bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

Examples of suitable salts include the hydrochloride salt, hydrobromide salt, sulphate salt, phosphate salt, nitrate salt and salts with sulphonic acids, e.g. methane sulphonic acid. Other suitable salts include organic salts such as acetate, citrate and fumarate.

Any of the PDE2 inhibitor compounds herein described may alternatively be provided in the form of a prodrug. The term "prodrug" refers to a derivative of an active compound which undergoes a transformation under the conditions of use, for example within the body, to release an active drug. A prodrug may, but need not necessarily, be pharmacologically inactive until converted into the active drug. As used herein, the term "prodrug" extends to any compound which under physiological conditions is converted into any of the active PDE2 inhibitor compounds herein described. Suitable prodrugs include compounds which are hydrolyzed under physiological conditions to the desired PDE2 inhibitor.

Prodrugs may typically be obtained by masking one or more functional groups in the parent molecule which are considered to be, at least in part, required for activity using a progroup. By "progroup" as used herein is meant a group which is used to mask a functional group within an active drug and which undergoes a transformation, such as cleavage, under the specified conditions of use (e.g. administration to the body) to release a functional group and hence provide the active drug. Progroups are typically linked to the functional group of the active drug via a bond or bonds that are cleavable under the conditions of use, e.g. in vivo.

Cleavage of the progroup may occur spontaneously under the conditions of use, for example by way of hydrolysis, or it may be catalyzed or induced by other physical or chemical means, e.g. by an enzyme, by exposure to a change in temperature, or to a change in pH, etc. Where cleavage is induced by other physical or chemical means, these may be endogenous to the conditions of use, for example pH conditions at the target site, or these may be supplied exogenously.

A wide variety of progroups suitable for masking functional groups in active compounds to provide prodrugs are well known in the art. For example, a hydroxy functional group may be masked as an ester, a phosphate ester, or a sulfonate ester which may be hydrolyzed in vivo to provide the parent hydroxy group. An amide functional group may be hydrolyzed in vivo to provide the parent amino group. A carboxyl group may be masked as an ester or amide which may be hydrolyzed in vivo to provide the parent carboxyl group. Other examples of suitable progroups will be apparent to those of skill in the art. The precise nature of the progroup may be selected according to need, for example depending on the desired oil or water solubility of the prodrug, its intended mode of administration and/or its intended mode of metabolism at the target site to produce the active drug compound. The progroup may, for example, be hydrophilic or lipophilic in order to increase or decrease water solubility as required. The choice of progroup may also impart other desirable properties such as enhanced absorption from the gastrointestinal tract, improved drug stability, etc.

The PDE2 inhibitors herein described are suitable for use in the treatment of tachycardia or tachyarrhythmia. For example, these may be used in the treatment of any of the following disorders: atrial tachycardia, atrial fibrillation, atrial flutter, paroxysmal supraventricular tachycardia, premature ventricular contractions (PVCs), ventricular fibrillation and ventricular tachycardia. In a preferred embodiment, the compounds may be used in the treatment of ventricular tachycardia. The treatment of conditions associated with an arrhythmia forms a preferred aspect of the invention, for example tachyarrhythmia.

In one embodiment, the compounds herein described may thus be used in the treatment or prevention of any of the following conditions: atrial tachycardia, atrial fibrillation, atrial flutter, paroxysmal supraventricular tachycardia, premature ventricular contractions (PVCs), ventricular fibrillation and ventricular tachycardia, for example in the treatment or prevention of any such conditions associated with an arrhythmia.

In one embodiment, the PDE2 inhibitors described herein are intended for the treatment or prevention or ventricular tachycardia. Treatment of a subject to prevent ventricular tachycardia is a preferred embodiment of the invention. Suitable subjects (e.g. patients) for treatment include subjects diagnosed as susceptible to ventricular tachycardia, and subjects who have previously experienced at least one incidence of ventricular tachycardia and who are therefore susceptible to further attacks. Treatment of such subjects is intended to reduce, preferably to eliminate, the occurrence of further ventricular tachycardiac events.

Tachycardias or tachyarrhythmias (for example, ventricular tachycardia) may be acquired, or they may be congenital. For example, they may be associated with, or arise from, various disorders relating to the heart, including but not limited to any of the following: congenital heart failure, hypertension, a myocardial infarction (either during or following a myocardial infarction), congestive heart failure, reperfusion injury or damage, ischemia, angina, dilated cardiomyopathy, post infarction heart failure, atherosclerotic peripheral arterial disease, diabetes, hypertrophic cardiomyopathy, myocarditis, channelopathies (e.g. long QT syndrome, catecholaminergic polymorphic ventricular tachycardia (CPVT) or Brugada syndrome), restrictive cardiomyopathy, infiltrative cardiac disease (e.g. amyloidosis) and alveolar hypoxia leading to pulmonary hypertension and right ventricle failure.

As used herein, the terms "treatment", "treating" and "treat" include both therapeutic and preventative methods directed to the defined disease or disorder in a subject. Specifically, these include: (i) prevention of the disorder from occurring, or reduction of the risk that the disorder may occur, in particular when the subject may be predisposed to the disorder but has not yet been diagnosed as having it; (ii) inhibiting the disorder, in particular arresting its further development (progression) or delaying its onset; and (iii) relieving the disorder, in particular causing the regression of the disorder until a desired outcome is reached.

Subjects (e.g. patients) which may benefit from the treatment methods according to the invention include, but are not limited to, any of the following: subjects who have previously suffered a myocardial infarction; subjects who have heart failure; and subjects who may be predisposed to any of the tachycardia conditions herein described, e.g. subjects having a genetic predisposition to such conditions, e.g. to catecholaminergic polymorphic ventricular tachycardia (CPVT) in which an abnormally fast and irregular heartbeat (tachycardia) is triggered in response to physical activity or emotional stress. Subjects suffering from any of the following conditions, or who may be predisposed to any of the following conditions, are particularly suited to treatment according to the methods herein described: heart failure, post-myocardial infarction, myocarditis, hypertrophic cardiomyopathy, CPVT, long QT syndrome and Brugada syndrome. A preferred group of subjects (e.g. patients) which may be treated in accordance with the invention include those suffering from, or at risk from, heart failure, CPVT or long QT syndrome.

In an embodiment, the invention relates to the treatment and/or prevention of ventricular tachycardia in subjects (e.g. human patients) suffering from any of the following conditions, or who may be predisposed to any of the following conditions: heart failure, post-myocardial infarction, myocarditis, hypertrophic cardiomyopathy, CPVT, long QT syndrome and Brugada syndrome.

CPVT and long QT syndrome are genetic syndromes with high risk of ventricular tachycardia. Nearly all patients with these conditions currently receive some form of anti-arrhythmic treatment. Although heart failure encompasses a diverse range of conditions, there can often be an associated risk of ventricular tachycardia. In particular, the invention relates to the treatment and/or prevention of ventricular tachycardia in subjects suffering from, or at risk from, heart failure, CPVT or long QT syndrome.

Subjects who may be predisposed to tachycardia (e.g. ventricular tachycardia) include those who have previously been diagnosed and/or treated for cardiac arrhythmias (e.g. ventricular tachycardias), for example subjects who have been prescribed anti-arrhythmic drugs such as beta-blockers to manage an abnormal heart rhythm, or subjects who have an implanted cardiac defibrillator (ICD). Symptomatic heart failure patients who have an ICD may particularly benefit from the treatment methods herein disclosed.

ICDs are typically implanted in patients having a high risk of ventricular tachycardia and/or sudden cardiac death, for example patients with heart failure or long QT syndrome. Within 1 to 3 years of implantation of the device, 20-35% of patients will experience an appropriate shock, i.e. the ICD converts a potentially lethal ventricular tachycardia to a normal heart rhythm. However, a third of patients may also experience an inappropriate shock, i.e. the ICD gives an unnecessary shock. Whenever the ICD shocks, this is associated with a 2-5 fold increase in mortality due to reduced heart function. It is therefore important to be able to reduce the amount of inappropriate ICD shocks to which a patient may be subjected. This can be achieved by the use of effective medication to treat or prevent the underlying heart condition, e.g. ventricular tachycardia. In one embodiment, the methods herein described may thus be used to treat or prevent ventricular tachycardia in patients having an implanted ICD and, in particular, to reduce or minimise the number of inappropriate ICD shocks to which the patient may be subjected.

Subjects undergoing long term treatment for a cardiac arrhythmia such as ventricular tachycardia (e.g. those who have been prescribed beta-blockers for at least 6 months, or at least 12 months) may particularly benefit from the treatment methods herein described. Although beta-blockers may typically be the first line treatment for ventricular tachycardias, their efficacy varies between conditions and in different patients. The methods herein described find particular use in the treatment of patients for whom conventional treatments (e.g. treatment with beta-blockers) is not sufficient to treat cardiac arrhythmias (especially ventricular tachycardias), or in cases where conventional drugs (e.g. beta-blockers) are either contraindicated (e.g. AV block) or not tolerated by the subject.

In one embodiment, the treatment methods may be used to treat patients with ICDs in order to minimise VA-induced symptoms and/or to reduce inappropriate ICD shocks (which is particularly common in CPVT, for example).

In one embodiment, the treatment methods may be used to treat patients with ICDs who are also undergoing conventional treatment for a cardiac arrhythmia, such as ventricular tachycardia. Such patients include those having an ICD and who are undergoing treatment with a beta-blocker (e.g. those who have been prescribed beta-blockers for at least 6 months, or at least 12 months).

As used herein, a "therapeutically effective amount" relates to an amount that will lead to the desired pharmacological and/or therapeutic effect, i.e. an amount of the PDE2 inhibitor which is effective to achieve its intended purpose. While individual patient needs may vary, determination of optimal ranges for effective amounts of the active agent is within the capability of one skilled in the art. Generally, the dosage regimen for treating a disease or condition with any of the compounds described herein is selected in accordance with a variety of factors including the nature of the medical condition and its severity.

As used herein, "subject" will typically be a mammal. The term "mammal" includes, for example, dogs, cats, cows, sheep, horses and humans. Preferably the subject will be a human.

The PDE2 inhibitors herein described will typically be administered in the form of a pharmaceutical composition. Pharmaceutical compositions may be formulated in conventional manner using readily available ingredients. Thus, the PDE2 inhibitor may be incorporated with one or more conventional carriers, diluents and/or excipients, to produce a pharmaceutical composition such as conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, etc.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used. The compositions may additionally include lubricating agents, wetting agents, viscosity increasing agents, colouring agents, granulating agents, disintegrating agents, binding agents, osmotic active agents, emulsifying agents, suspending agents, preserving agents, sweetening agents, flavouring agents, adsorption enhancers, e.g. for nasal delivery (bile salts, lecithins, surfactants, fatty acids, chelators) and the like. The pharmaceutical compositions may be formulated so as to provide quick, sustained or delayed release of the PDE2 inhibitor after administration to the patient by employing procedures well known in the art.

The active ingredient (i.e. the PDE2 inhibitor) in such compositions may comprise from about 0.01% to about 99% by weight of the formulation, preferably from about 0.1 to about 50%, for example 10% by weight.

The administration may be by any suitable method known in the medicinal arts, including for example oral, parenteral (e.g. intramuscular, subcutaneous, intraperitoneal or intravenous), percutaneous, buccal, rectal or topical administration, or administration by inhalation. The preferred routes of administration are oral and parenteral (e.g. intravenous or intraperitoneal). Preferred formulations for use in the invention are thus tablets, capsules or intravenous solutions.

Tablets are typically prepared by direct compression or a granulation procedure, for example using standard fluid bed technology. The tablets are preferably coated with a film coating or another coating such as an enteric coating. The capsules are preferably gelatine capsules. A composition for injection can be a ready to use solution or a dry material to be dissolved before administration. All intravenous compositions are sterile. Any sterilisation method may be used, such as heat sterilisation and aseptic preparation.

The unit dose will vary depending upon the chosen PDE2 inhibitor and the disease or disorder being treated. Typically, the unit dose will vary from 0.1 mg to 500 mg; more preferably from 1 mg to 300 mg. A typical daily dose may be from 0.1 mg to 2 grams, more preferably 1 mg to 1 g, e.g. 1 mg to 600 mg.

Typical daily doses per kg body weight of the subject may vary from 0.01 mg/kg to 50 mg/kg, preferably from 0.1 mg/kg to 40 mg/kg, e.g. from 1 mg/kg to 20 mg/kg or from 5 mg/kg to 10 mg/kg.

The dosing regime will vary depending upon the clinical situation. Typical average dosing will be once, twice or three times a day, preferably once or twice a day.

The precise dosage of the active compound to be administered and the length of the course of treatment will be dependent on a number of factors including for example, the age and weight of the subject, the specific condition requiring treatment and its severity, and the route of administration. Suitable dosages can readily be determined by those of skill in the art.

PDE2 inhibition as an anti-arrhythmia treatment as herein described may be used alone, for example where this is more effective than known treatment options (e.g. treatment with beta-blockers) and/or where current treatments are not relevant, for example where these may be contraindicated in any given patient group. Alternatively, any of the methods of treatment herein described may advantageously be combined with administration of one or more additional active agents which are effective in treating the disorder or disease to be treated, i.e. as an add-on therapy to current regimes). Such treatment methods may involve simultaneous, separate or sequential administration of the PDE2 inhibitor, or a pharmaceutical composition containing the PDE2 inhibitor, and the additional active agent. Where the actives are to be administered simultaneously, these may be provided in the form of a combined preparation. Thus, the pharmaceutical compositions herein described may additionally contain one or more of such active agents.

Other active agents which may be co-administered with the PDE2 inhibitor may include cardiovascular drugs. For example, the PDE2 inhibitor may be co-administered with one or more drugs that treat hypertension, heart failure, arrhythmia and/or post infarction myocardial reperfusion syndrome. Examples of such drugs include beta-blockers, calcium antagonists, ACE-inhibitors, ATII/-blockers and anti-arrhythmic drugs. In one embodiment, the cardiovascular drug may be a beta-blocker, for example a $\beta_1$-selective beta-blocker such as acebutolol, atenolol, betaxolol, bisoprolol, celiprolol, metoprolol, nebivolol or esmolol. In a particular embodiment, metoprolol may be co-administered with a PDE2 inhibitor in the treatment or prevention of any of the conditions herein described, in particular in the treatment or prevention of ventricular tachycardia.

The following Examples are given by way of illustration only and with reference to the accompanying figures in which:

FIG. 1: NKA currents are regulated by cAMP and local AKAP-bound PKA. A) Outline of protocol for NKA current measurements. Isolated cardiomyocytes were voltage clamped at −20 mV and externally superfused and internally dialyzed with solutions with symmetrical Na$^+$ concentrations (left panel). NKA currents were measured by removing K$^+$ from the superfusate (right panel). B) Effect of increasing concentrations of cAMP on NKA currents. *=p<0.05 to 0 cAMP. 6-13 ARVMs from 2-5 rats. C) Effect of 20 μM superAKAP on the NKA current. 6-7 ARVMs from 2 rats. *=p<0.05 to 100 μM cAMP.

FIG. 2: PDE2 regulates NKA activity. A) Effect of three different PDE2 inhibitors on the NKA current. 5-8 ARVMs from 3 rats. NKA currents from control vs Bay 60-7550 and control vs PF05180999 are paired. *=p<0.05 to control. B) NKA currents in PDE2KO vs WT mice. 7-8 myocytes from 3 mice. *=p<0.05 to WT. C) Effect of PDE3 and PDE4 inhibition on the NKA current. D) Phosphorylation at ser68 on phospholemman (PLM) after treatment with isoprenaline and PDE inhibitors.

FIG. 3: NKA and PDE2 colocalize and interact. A-B) Proximity ligation assay of NKA and PDE2 in ARVMs. *=p<0.05 to experiments with no or single antibody. C) Co-immunoprecipitation of NKA and PDE2 in HEK293 cells.

FIG. 4: PDE2 inhibition reduces Ca$^{2+}$ transient amplitude and SR Ca$^{2+}$ load. A) Effect of Bay 60-7550 on Ca$^{2+}$ transient amplitude (left) (12 ARVMs from 3 rats), Ca$^{2+}$ extrusion rate (middle) (12 ARVMs from 3 rats) and SR Ca$^{2+}$ load (right) (11 ARVMs from 3 rats) in ARVMs. *=p<0.05 to control. B-C) Representative tracings of Bay 60-7550 effect on Ca$^{2+}$ transients (B) and tracing showing typical caffeine response (C). D) Ca$^{2+}$ transient amplitude (left) (14-16 myocytes from 3 mice), Ca$^{2+}$ extrusion rate (middle) (14-16 myocytes from 3 mice) and SR Ca$^{2+}$ load (right) (11-14 myocytes from 3 mice) in PDE2KO vs WT. *=p<0.05 to WT.

FIG. 5: PDE2 inhibition increases NCX-dependent Ca$^{2+}$ extrusion. A) Representative tracings of showing protocol for measurements of the activity of the main Ca$^{2+}$ extruding proteins. B) Effect of Bay 60-7550 on SERCA2 activity (left) (10 ARVMs from 3 rats), NCX activity (middle) (11 ARVMs from 3 rats) and non-SERCA2/non-NCX Ca$^{2+}$ extrusion (right) (5 ARVMs from 2 rats). *=p<0.05 to control. C) SERCA2 activity (left) (10-14 myocytes from 3 mice), NCX activity (middle) (10-14 myocytes from 3 mice) and non-SERCA2/non-NCX Ca$^{2+}$ extrusion (right) (4-5 myocytes from 3 mice) in PDE2KO vs WT. *=p<0.05 to WT. D) Intracellular Na$^+$ measured with SBFI. Representative tracings (left) and average data (right). 6 ARVMs from 3 rats.

FIG. 6: No effect of PDE2 inhibition on LTCC and RyR activity. A-B) Representative tracings (A) and average data (B) of LTCC with Bay 60-7550 treatment. 5 ARVMs from 3 rats. C-D) Representative tracings (C) and average data (D) of Ca$^{2+}$ sparks frequency with Bay 60-7550 treatment. 6 ARVMs from 2 rats. E) Average data of Na$^+$ current with Bay 60-7550. 6-7 ARVMs from 3 rats.

Figure 7:
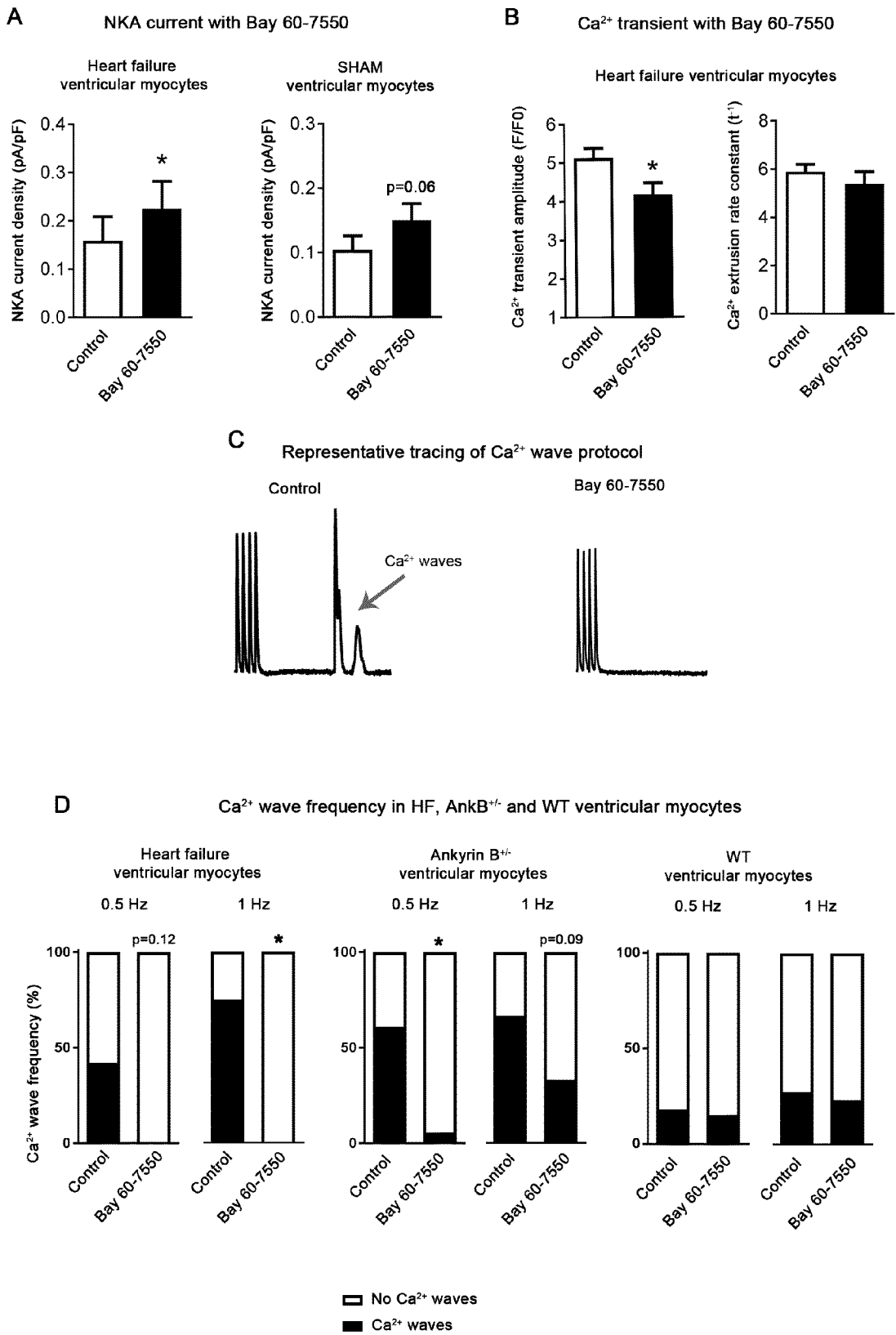

FIG. 7: PDE2 inhibition reduces cellular arrhythmias in post-banding HF and AnkB$^{+/-}$. A) NKA current with Bay 60-7550 in myocytes from post-banding HF (6 myocytes from 3 mice) and SHAM (2 myocytes from 1 mouse). *=p<0.05 to control. B) Effect of Bay 60-7550 on Ca$^{2+}$ transient amplitude (left) (11-12 myocytes from 3 mice) and Ca$^{2+}$ extrusion rate (right) (10-12 myocytes from 3 mice) in post-banding HF myocytes. *=p<0.05 to control. C) Representative tracing of protocol for detecting Ca$^{2+}$ waves from post-banding HF myocytes. D) Ca$^{2+}$ wave frequency in isolated myocytes from post-banding HF mice (11-12 myocytes from 3 mice), AnkB$^{+/-}$ mice (18 myocytes from 3 mice) and WT (AnkB$^{+/+}$) mice (11-13 myocytes from 3 mice). *=p<0.05 to control.

Figure 8:
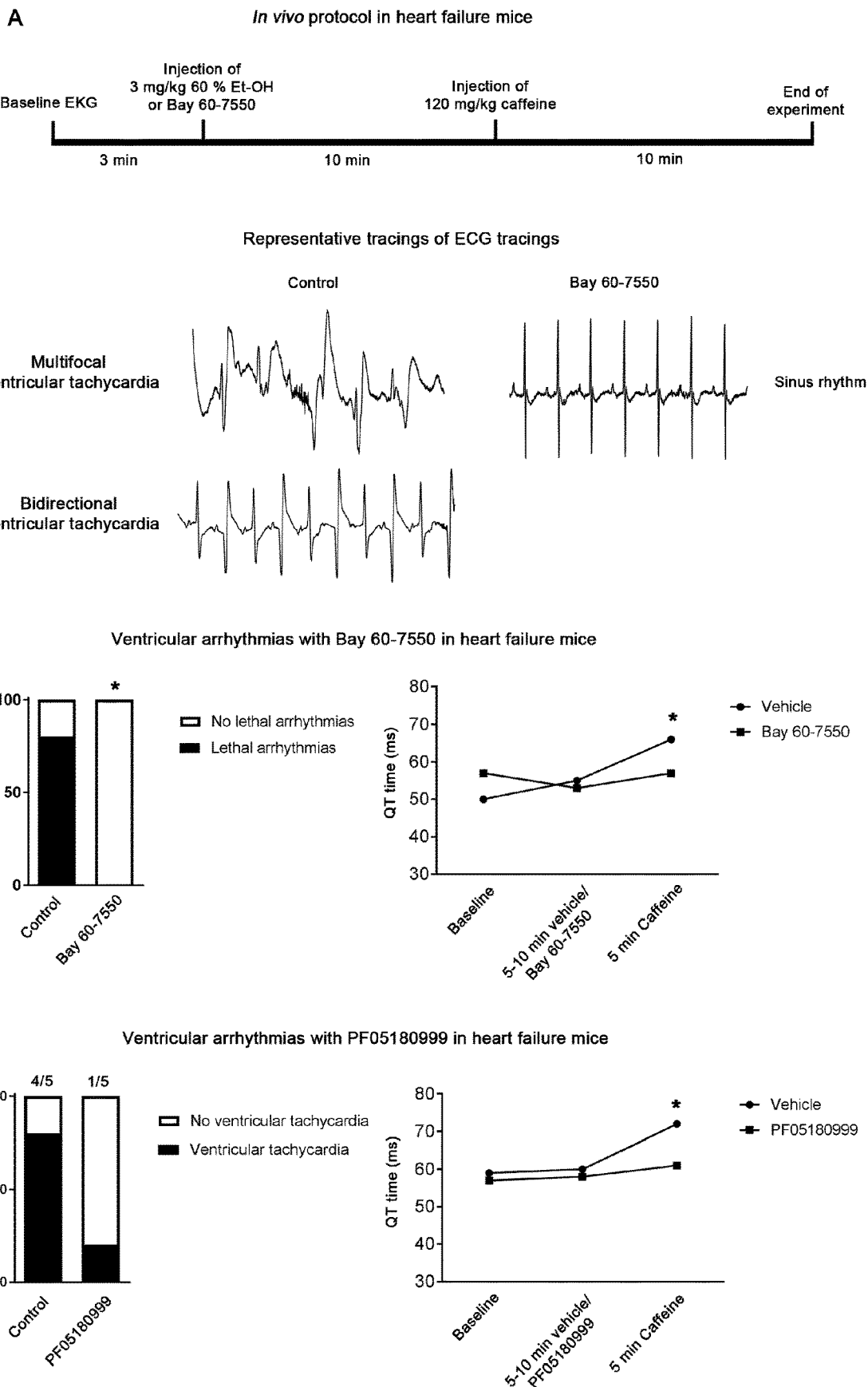

FIG. 8: PDE2 inhibition protects against ventricular tachycardia and death in post-banding HF mice. A) Protocol for in vivo arrhythmias in post-banding HF mice. B) Representative ECG tracings from HF mice showing examples of VTs (bidirectional VT and multifocal VT) and sinus rhythm. C) Ventricular tachycardia and death (left) and QT time (right) with Bay 60-7550 in HF mice (n=5 in both groups). *=p<0.05 to vehicle. D) Ventricular tachycardia (left) and QT interval (right) with PF05180999 in HF mice (n=5 in both groups).

FIG. 9: PDE2 inhibition protects against ventricular tachycardia in AnkB$^{+/-}$ mice. A) Protocol for in vivo arrhythmias in AnkB$^{+/-}$ mice. B) Ventricular tachycardia (left) and QT interval (right) with Bay 60-7550 in AnkB$^{+/-}$ mice (n=8 in both groups). *=p<0.05 to vehicle. D) Ventricular tachycardia (left) and QT interval (right) with PF05180999 in AnkB$^{+/-}$ mice (n=5 in both groups). *=p<0.05 to vehicle.

Figure 10:
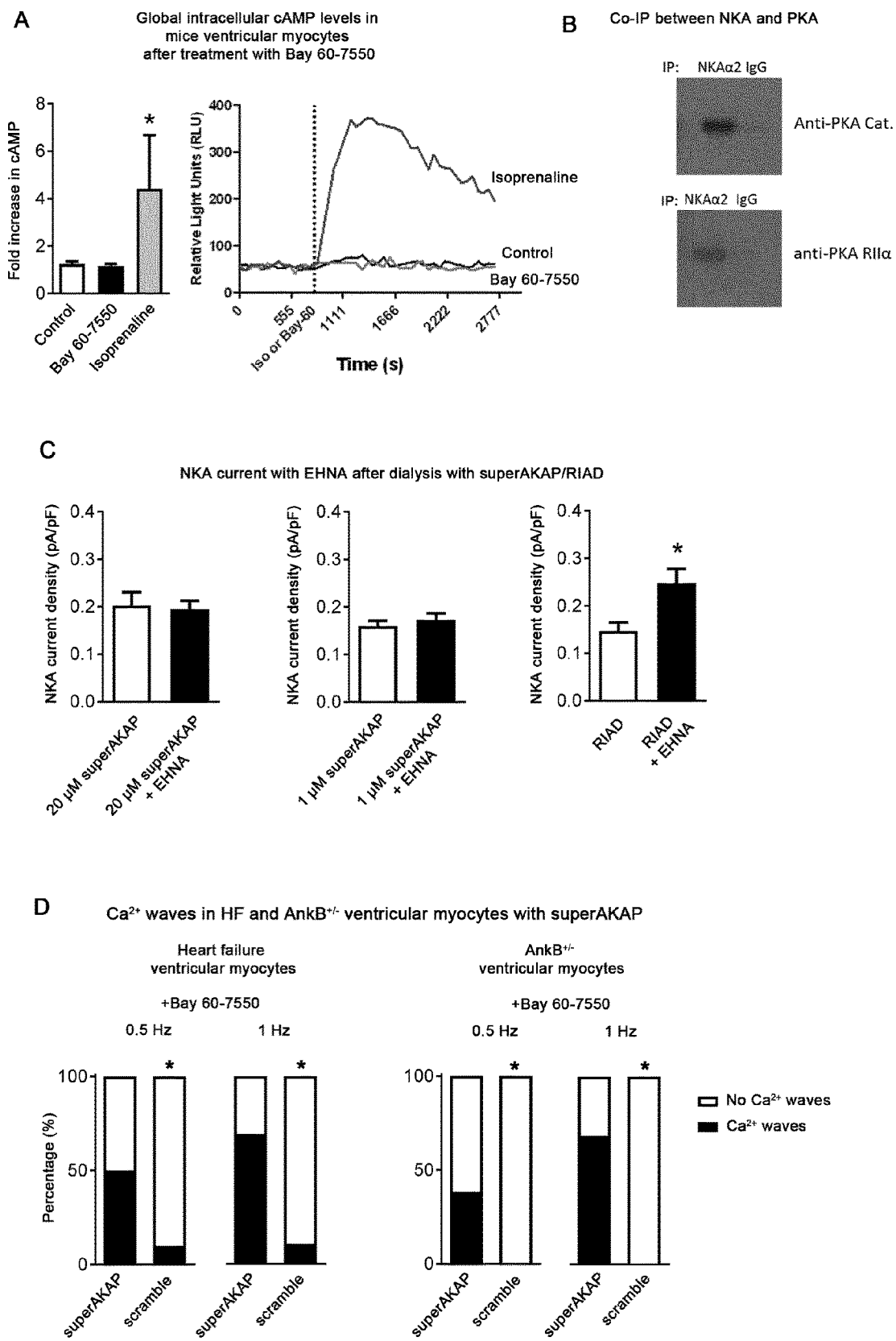

FIG. 10: PDE2 inhibition increases NKA current and prevent cellular arrhythmias through local pools of cAMP. A) Average data (left) and representative tracing (right) showing global intracellular cAMP levels in ventricular myocytes from mice after treatment with Bay 60-7550 (2 mice, 2 repeats per mouse). Isoprenaline was used as a positive control. B) Co-immunoprecipitation between NKA and PKA catalytic site and PKA RII. C) NKA currents with EHNA after treatment with superAKAP/RIAD (5-8 ARVMs from 3 rats). *=p<0.05 to RIAD. D) $Ca^{2+}$ waves in myocytes with Bay 60-7550 from post-banding HF mice (10-14 myocytes from 3 mice) and AnkB$^{+/-}$ mice (10-13 myocytes from 2 mice) after pre-treatment with superAKAP. *=p<0.05 to superAKAP.

FIG. 11: PDE2 inhibition no longer protects against ventricular tachycardia in post-banding HF mice and AnkB$^{+/-}$ mice after pre-treatment with superAKAP. A) Protocol for in vivo arrhythmias in post-banding HF mice and AnkB$^{+/-}$ mice with Bay 60-7550 and superAKAP/scramble. B) Ventricular tachycardia (left) and QT interval (right) with Bay 60-7550 and superAKAP/scramble in HF mice (n=6 in both groups). *=p<0.05 to vehicle. D) Ventricular tachycardia (left) and QT interval (right) with with Bay 60-7550 and superAKAP/scramble in AnkB$^{+/-}$ mice (n=5 in both groups).

FIG. 12: Proposed mechanism for local PDE2 regulation of NKA. A) We propose that PDE2 and NKA assemble in a common domain, where PDE2 locally regulates cAMP levels and AKAP-bound PKA-RII activity. PKA-RII phosphorylates phospholemman, which regulates NKA activity. B) With superAKAP, which disrupts PKA-RII from AKAPs, PDE2 is no longer able to regulate NKA.

Figure 13:
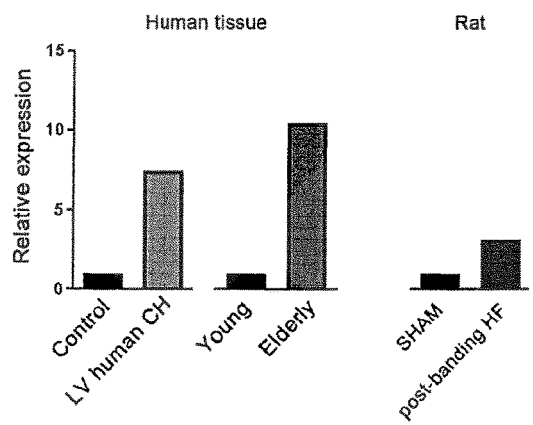

FIG. 13: Increased PDE2-mRNA expression in human cardiac hypertrophy and ageing and in rat post-banding HF. Data from mRNA sequencing from isolated and sorted cardiomyocyte nuclei.

Figure 14:
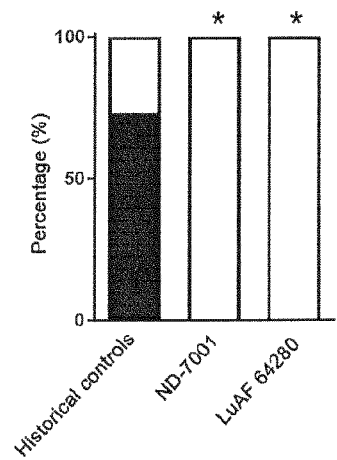

FIG. 14: PDE2 inhibition protects against ventricular tachycardia in post-banding HF mice. Ventricular tachycardia with historical controls (n=15), ND-7001 (n=5) and LuAF64280 (n=3) in HF mice. *=p<0.05 to control.

Figure 15:
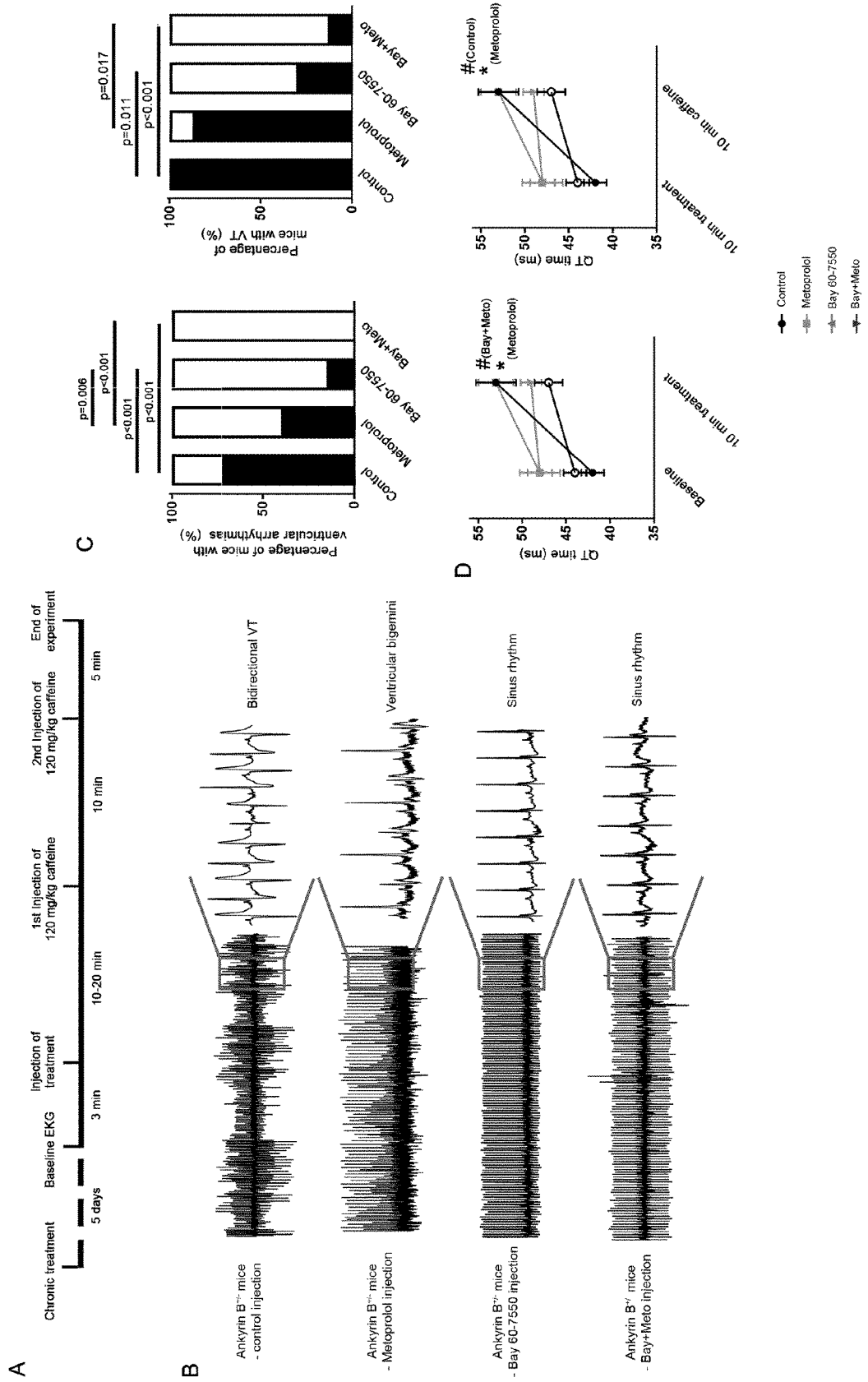

FIG. 15: PDE2 inhibition is superior to beta-blockers in preventing Ca2+-induced ventricular arrhythmias A) Protocol for chronic benchmarking study in AnkB+/− mice. B) Representative tracings of ECG recordings in the four treatment groups. C) Average data showing presence of ventricular tachyarrhythmias and ventricular tachycardias in the four treatment groups. Control 11 mice, Metoprolol 15 mice, Bay 60-7550 13 mice, Bay 60-7550+Metoprolol 15 mice. D) QT time in the four treatment groups with injection of treatment (left) or caffeine (right). *=p<0.05. #=p<0.01.

Figure 16:
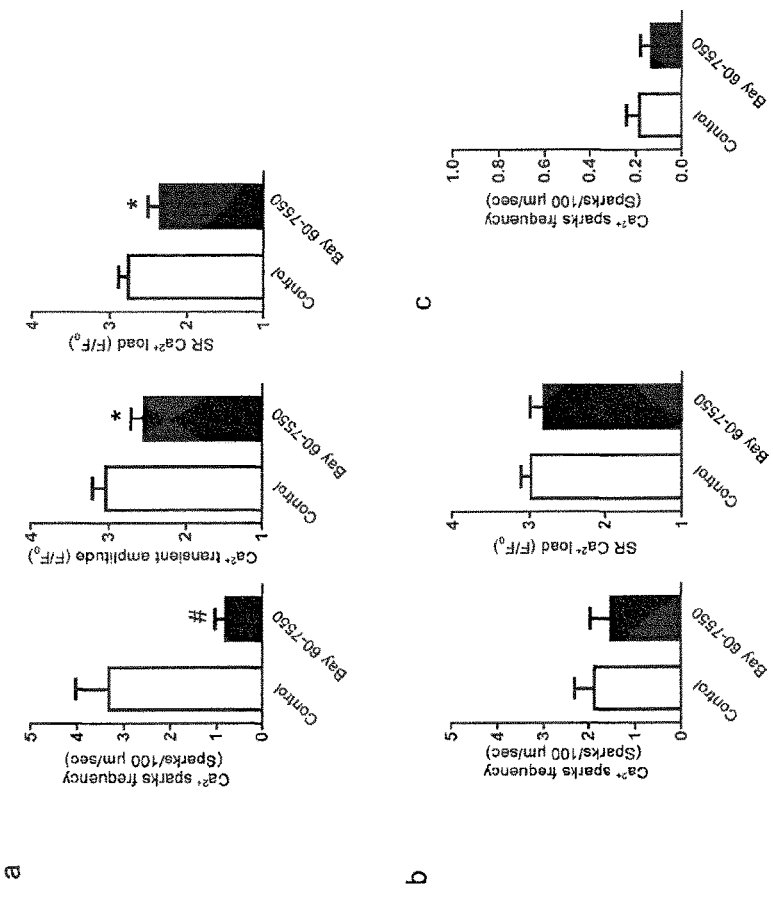

FIG. 16: No effect of PDE2 inhibition RyR activity. A) Representative tracings and average data of PDE2 inhibition on $Ca^{2+}$ spark frequency, $Ca^{2+}$ transient amplitude and SR $Ca^{2+}$ load in field stimulated ARVMs. 18 ARVMs from 3 rats. *=p<0.05 to control. B) Representative tracings and average data of PDE2 inhibition on $Ca^{2+}$ spark frequency and SR $Ca^{2+}$ load in non-stimulated ARVMs. 19 (Bay 60-7550) and 22 (control) ARVMs from 3 rats. C) Representative tracings and average data of PDE2 inhibition on $Ca^{2+}$ spark frequency in saponin-permeabilized ARVMs. 25 (Bay 60-7550) and 24 (control) ARVMs from 3 rats.

Figure 17:
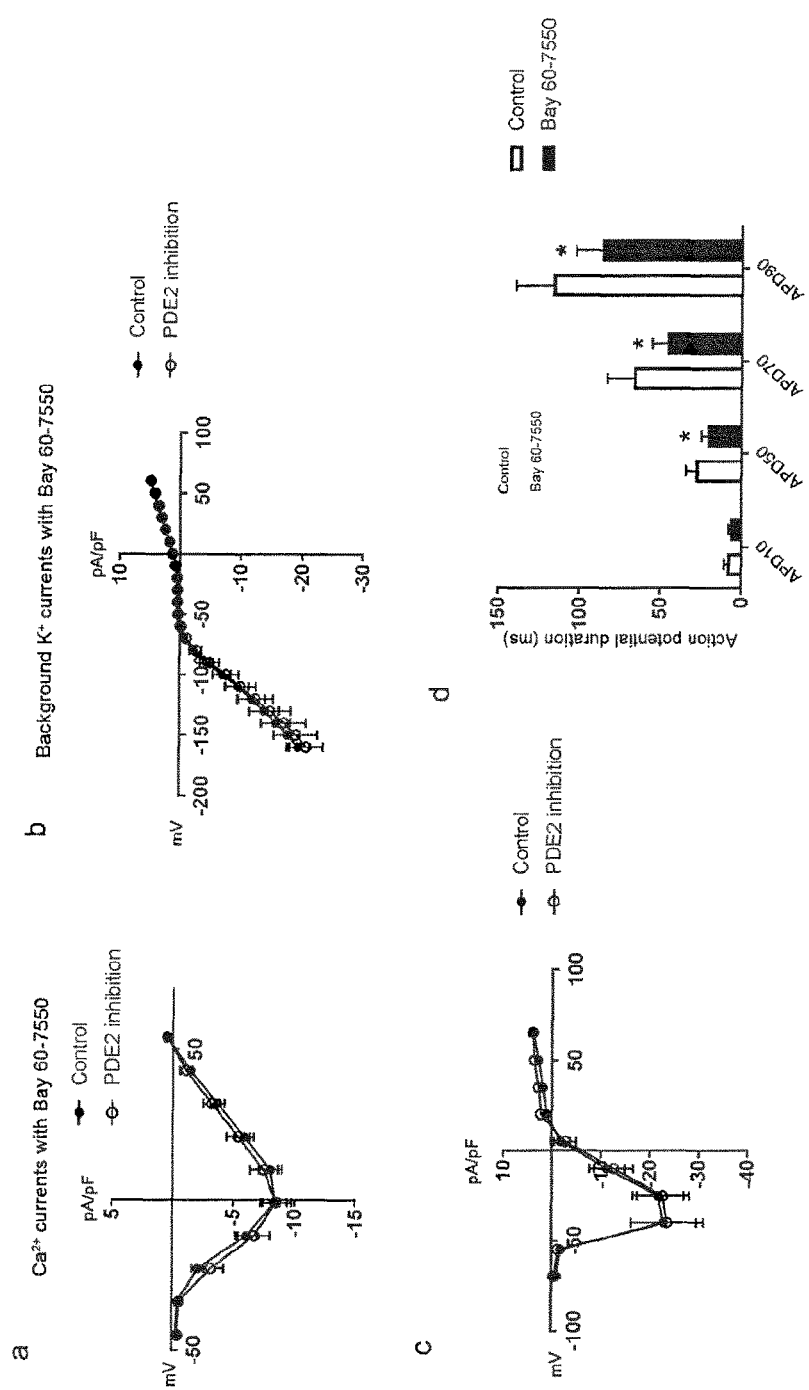

FIG. 17: PDE2 inhibition has no effect on other anti-arrhythmic targets. A) Effect of PDE2 inhibition on LTCC. 8 (control) and 10 (Bay 60-7550) ARVMs from 3 rats (both groups). B) Effect of PDE2 inhibition on background K+ currents 7 (both groups) ARVMs from 3 rats. C) Effect of PDE2 inhibition on Na$^+$ currents. 7 (control) and 8 (Bay 60-7550) ARVMs from 3 rats. D) Effect of PDE2 inhibition on action potential duration. *=p<0.05 vs control.

FIG. 18: PDE2 inhibition protects against ventricular tachycardia in CPVT mice. Ventricular tachycardia with controls (n=6) and Bay 60-7550 (n=7) in CPVT mice. *=p<0.05 vs control.

EXAMPLES

Example 1

The following methods were carried out to demonstrate that phosphodiesterase 2A inhibition activates the Na$^+$/K$^+$-ATPase and prevents ventricular tachycardias.
Methods:
Animal Models Animal experiments were performed in accordance with the Guide for the Care and Use of Laboratory Animals published by the US National Institutes of Health (NIH Publication No.85-23, revised 1996). Project approval was granted by the Norwegian National Animal Research Committee (FDU 2146, 7016 and 7040). Male Wistar rats with ~300 g body weight (Møllegaard, Denmark) were stored two per cage in a temperature-regulated room on a 12:12 h day/night cycle and given access to food and water ad libitum. Mice were stored under similar conditions, and maximally six mice per cage were allowed. Aorta banding was performed in C57BL6/J mice by a standardized constriction of the ascending aorta, and the mice were followed for 14-16 weeks. Development of congestive heart failure was verified by echocardiography and post-mortem examination as previously described (Aronsen, J. M., et al., *Noninvasive stratification of postinfarction rats based on the degree of cardiac dysfunction using magnetic resonance imaging and echocardiography*. American Journal of Physiology-Heart and Circulatory Physiology, 2017. 312(5): H932-H942). Ankyrin B$^{+/-}$ mice were bred as previously described (Mohler, P. J., et al., *Ankyrin-B mutation causes type 4 long-QT cardiac arrhythmia and sudden cardiac death*. Nature, 2003. 421(6923): 634-9). Floxed PDE2A mice were crossed with alpha-MHC MerCreMer mice and were used to test the cardiomyocyte specific role of PDE2A with methods as previously described (Hougen, K., et al., *Cre-loxP DNA recombination is possible with only minimal unspecific transcriptional changes and without cardiomyopathy in Tg(alpha MHC-MerCreMer) mice*. American Journal of Physiology-Heart and Circulatory Physiology, 2010. 299(5): H1671-H1678).
Cell Isolation Male Wistar rats were anaesthetized in 4% isoflurane, 65% $N_2O$ and 31% $O_2$, and intubated and ventilated with 2% isoflurane, 66% $N_2O$ and 32% $O_2$. Deep surgical anesthesia was confirmed by abolished pain reflexes. 150 IE heparin was administrated intravenously for post-excision thrombosis prophylaxis. The heart was excised and immediately cooled in 0.9% NaCl at 4° C. Aorta was cannulated and the coronary arteries retrogradely perfused in a modified Langendorff setup with buffer A (in mM: Hepes 25, NaCl 130, KCl 5.4, $NaH_2PO_4$ 0.4, $MgCl_2$ 0.5, D-glucose 22, pH 7.4) at 37° C. for 2-4 min, then with buffer A containing 0.8 g/L collagenase II (Worthington Biochemical Corporation, USA) and 6.7 μM $CaCl_2$ for 18-22 min. Atria and the right ventricular free wall were removed before the LV was cut into small pieces in 8-10 mL of the perfusate added 500 μL 2% BSA, and mechanically isolated by careful pipetting with a Pasteur pipette for 1 min. The cardiomyocyte suspension was filtered through a nylon mesh (200 μm, Burmeister, Lørenskog, Norway), and left at room temperature for sedimentation. Immediately following sedimentation (~5 min), the supernatant was removed. For single-cell experiments and generation of primary cultures for cAMP measurements, the cardiomyocytes were washed three times in buffer A containing 1) 0.1% BSA and 0.1 mM $CaCl_2$, 2) 0.1% BSA and 0.2 mM $CaCl_2$, and 3) 0.05% BSA and 0.5 mM $CaCl_2$. For generation of primary cultures for proximity ligation assay, the cardiomyocytes were washed three times in buffer A with decreasing concentration of BSA (0.1%, 0.05% and 0%).

Left ventricular myocytes from PDE2-deficient mice, $Ankyrin^{+/-}$ mice and C57BL6/J mice after sham or AB operation were isolated based on a similar protocol as recently described (Ackers-Johnson, M., et al., *A Simplified, Langendorff-Free Method for Concomitant Isolation of Viable Cardiac Myocytes and Nonmyocytes From the Adult Mouse Heart*. Circ Res, 2016. 119(8): 909-20). Mice were anesthetized in a combination of 5% isoflurane and 95% $O_2$, and mask ventilated by a combination of 5% isoflurane and 95% $O_2$. Deep surgical anesthesia was confirmed by abolished pain reflexes. The chest was opened, before the descending aorta and inferior caval vein was cut. 7 mL of buffer A with 5 mM EDTA was injected into the right ventricle. Thereafter, the aorta was clamped and the heart was excised. 10 mL of the buffer solution and thereafter 3 ml of the buffer solution without EDTA was injected into the left ventricle over 2-5 min. Then preheated solution A containing 0.8 mg/mL collagenase II was injected into the left ventricle over ~20 min. The atria and right ventricle was removed, and the remaining procedure was similar the procedure described for the Langendorff-based isolation above.

Proximity Ligation Assay

Isolated cardiomyocytes were washed twice in PBS at room temperature, transferred to 4% paraformaldehyde (PFA) and gently shaken for 30 min, then washed twice again in PBS. The cardiomyocyte suspension was next transferred to 0.8 $cm^2$ wells, each coated with 8 µg laminin (Invitrogen), and incubated at 37° C. for 2 h. PBS was replaced by 0.1% Triton X100 in PBS, and incubated for 10 min at 37° C. Proximity ligation assay was then performed with the Duolink II proprietary system (Olink Bioscience, Uppsala, Sweden), according to the manufacturer's protocol (Soderberg, O., et al., *Direct observation of individual endogenous protein complexes in situ by proximity ligation*. Nat Methods, 2006. 3(12): 995-1000).

Cardiomyocytes were scanned on a Zeiss LSM 710 confocal microscope (excitation 543 nm HeNe laser, through a MBS 488/543 dichroic mirror, emission collected at 565-589 nm). ImageJ 1.44p software (http://imagej.nih.gov/ij) was used for analysis of single-cell intracellular fluorescence intensity by measuring whole cell mean gray value. Results were corrected for background fluorescence signal.

Whole-Cell Voltage Clamp Experiments

Whole-cell continuous voltage clamp was performed in isolated cardiomyocytes, using an Axoclamp 2B or 2A amplifier and pCLAMP software (both Axon Instruments, Foster City, Calif., USA). The signal was sampled at 10 kHz and filtered with a low-pass filter before analysis. All amplifier and program settings were held constant during and between experiments. The cells were superfused at 37° C., and the superfusion system was arranged to allow rapid switch of solution.

NKA Currents:

Wide tipped patch pipettes (1.5-2.5 MΩ) were filled with internal solution (in mM, modified from Despa, S. and D. M. Bers, *Na/K pump current and [Na](i) in rabbit ventricular myocytes: local [Na](i) depletion and Na buffering*. Biophys J, 2003. 84(6): 4157-66.: NaCl 17, KCl 13, K-Aspartate 85, TEA-Cl 20, HEPES 10, MgATP 5, $MgCl_2$ 0.7 (free $Mg^{2+}$ ~1.0 mM using Maxchelator, Stanford), BAPTA 3, $CaCl_2$ 1.15 (free $Ca^{2+}$ 150 nM), pH=7.2 (adjusted with KOH). After reaching whole-cell access, the cells were dialyzed for at least 4 minutes at −20 mV. Holding potential in the remaining experiment was −20 mV. The series resistance was 3-6 MΩ in most cells and any cell with a series resistance >9MΩ was discarded.

The cells were patched in solution A (mM): NaCl 140, Hepes 5, KCl 5.4, $CaCl_2$ 1, $MgCl_2$ 0.5, D-glucose 5.5 and $NaH_2PO_4$ 0.4. pH was adjusted to 7.4. After reaching whole-cell access, cells were superfused with solution B (in mM): N-methyl-D-glucamine 108, NaCl 17, D-glucose 10, HEPES 5, KCl 15, $NiCl_2$ 5, $BaCl_2$ 2, $MgCl_2$ 1, pH adjusted to 7.4 HCl. 5 µM cAMP and peptides (1 or 20 µM super-AKAP or 1 µM RIAD) were added to the internal solution on experiment day. NKA currents were elicited by rapidly removing extracellular KCl (replaced with equal amounts of TrisCl). Solutions with symmetrical $Na^+$ concentrations were used (i.e. the same concentration of $Na^+$ in both the superfusate and the internal solution) in order to reduce the influence of intracellular $Na^+$ gradients on the NKA currents. 100 nM Bay 60-7550, 100 nM PF05180999 or 10 µM EHNA were added to the superfusate on the day of experiments to measure the effect of PDE2 inhibition on NKA currents. Both paired and unpaired recordings were performed, but with consistency within one data set. In the paired recordings, NKA currents during control conditions and with PDE2 inhibitor were measured in the same cell, but with at least 5 minutes between the recordings. We alternated whether the first recorded NKA current in one cell was with or without PDE2 inhibitor to minimize any unwanted time-dependent effects. NKA currents were related to cell capacitance to account for differences in cell size.

L-Type $Ca^{2+}$ Currents (LTCC):

Wide tipped patch pipettes (1.4-1.8 MΩ) were filled with internal solution (in mM, modified from Leroy, J., et al., *Phosphodiesterase 48 in the cardiac L-type Ca(2)(+) channel complex regulates Ca(2)(+) current and protects against ventricular arrhythmias in mice*. J Clin Invest, 2011. 121(7): 2651-61: CsCl 122, HEPES 10, MgATP 10, $MgCl_2$ 0.7 (free $Mg^{2+}$ ~0.6 mM), $Na_2$Phosphodicreatinine 5, EGTA 10, $CaCl_2$ 0.2 (free $Ca^{2+}$ 3 nM), pH 7.2 with CsOH. Series resistance was between 4-8 MΩ in all recordings. The holding potential was −45 mV, and $Ca^{2+}$ transients were triggered by a 100 ms square voltage step from −45 to 0 mV at 0.125 Hz. The cells were patched in solution A, but after whole-cell access was reached, solution C was applied (in mM, modified from Leroy, J., et al., *Phosphodiesterase 4B in the cardiac L-type Ca(2)(+) channel complex regulates Ca(2)(+) current and protects against ventricular arrhythmias in mice*. J Clin Invest, 2011. 121(7): 2651-61: NaCl 118, CsCl 20, D-glucose 5, $MgCl_2$ 1.8, HEPES 10, $NaH_2PO_4$ 0.8, $CaCl_2$ 1.8, pH 7.4 with NaOH. The internal solution was allowed to equilibrate for at least 4 minutes before recordings were started. No recordings were initiated before the LTCC were completely stable. Control recordings and recordings with Bay 60-7550 were performed in the same cell.

$Na^+$ Currents:

Low resistance pipettes (1.4-2.5 MΩ) were filled with internal solution (in mM, modified from Leroy, J., et al., *Phosphodiesterase 4B in the cardiac L-type Ca(2)(+) channel complex regulates Ca(2)(+) current and protects against ventricular arrhythmias in mice*. J Clin Invest, 2011. 121(7):

2651-61): CsCl 122, HEPES 10, MgATP 5, $MgCl_2$ 0.7 (free $Mg^{2+}$ ~0.6 mM), $Na_2$Phosphodicreatinine 5, EGTA 10, $CaCl_2$ 0.2 (free $Ca^{2+}$ 3 nM), pH 7.2 with CsOH. Series resistance was between 4-7.5 MΩ in all recordings. The cells were patched in solution A, but after whole-cell access was reached, solution D was applied: N-methyl-D-glucamine 125, NaCl 10, CsCl 5, D-glucose 5, $MgCl_2$ 1.2, HEPES 10, $NiCl_2$ 5, pH 7.4 with CsOH. 20 µM Nifedipine was added on experiment day to inhibit L-type $Ca^{2+}$ channels. Holding potential was −80 mV. $Na^+$ currents were measured in discontinuous mode (switching rate 9 kHz) by applying a 50 ms square voltage step from the holding potential of −80 mV to −10 mV at 1 Hz. Good voltage control was maintained by symmetrical $Na^+$ solutions and a low series resistance. A multistep protocol with −10 mV incremental steps ranging from −70 mV to +50 mV (all from the −80 mV holding potential) was run prior to these experiments to determine the test potential that yielded the largest peak current, with no difference between control and Bay 60-7550. The internal solution was allowed to equilibrate for at least 4 minutes before recordings were started. No recordings were initiated before the $Na^+$ currents were completely stable. Control recordings and recordings with Bay 60-7550 were mostly performed in separate cells. However, in a subset of cells, both control and Bay 60-7550 were recorded in the same cell.

Field Stimulation Experiments

Whole-Cell $Ca^{2+}$ Transients:

$Ca^{2+}$ transients were recorded in field stimulated myocytes loaded with 5 µM Fluo4-AM for 10-15 minutes (Molecular Probes, Eugene, USA), followed by 5 minutes de-esterification. Experiments were either performed with and without 100 nM Bay 60-7550 in the same cell (rat ventricular myocytes) or in PDE2KO or WT ventricular myocytes. In experiments with peptides, myocytes were incubated with either 1 µM TAT-conjugated peptides (superAKAP or corresponding scrambled peptide) for 20 minutes. During the recordings the myocytes were then superfused with solution A containing the same peptide.

Cellular fluorescence was obtained with Cairn Research Optoscan Monochromator (excitation 485 nm, emission 515 nm long pass) (Cairn Research Ltd., Faverham, UK). Cell-free fluorescence was obtained after each experiment and subtracted from the tracing to correct for background fluorescence. Cells were stimulated at 0.5 Hz for at least 3 minutes or until the $Ca^{2+}$ transients stabilized before recordings were initiated. Cells without stable $Ca^{2+}$ transients (both baseline and peak $Ca^{2+}$ levels) were discarded. Field stimulation was then stopped and a brief pulse of 10 mM caffeine was added. The SR $Ca^{2+}$ content was recorded as the peak of the caffeine-evoked $Ca^{2+}$ transient. The same experiment was performed after addition of 10 mM $Ni^{2+}$ in the superfusate to block NCX activity. Tau values were obtained by monoexponential fitting of the $Ca^{2+}$ extrusion phase from regular transients (T), caffeine transients ($T_{caff}$) and caffeine transients with $Ni^{2+}$ ($T_{Ni}$). SERCA2 rate constant was calculated as the difference between the rate constant for field stimulated $Ca^{2+}$ transients and the caffeine-evoked $Ca^{2+}$ transient (Trafford, A. W., M. E. Diaz, and D. A. Eisner, *Measurement of sarcoplasmic reticulum Ca content and sarcolemmal fluxes during the transient stimulation of the systolic Ca transient produced by caffeine*. Ann NY Acad Sci, 1998. 853: 368-71) while $T_{caff}$ was interpreted as $Ca^{2+}$ extrusion through NCX in absence of any difference in $T_{Ni}$.

Protocol for Detecting Cellular Arrhythmias:

Isolated ventricular myocytes from post-banding HF mice, AnkB$^{+/-}$ mice and WT (AnkB$^{+/+}$) were pre-conditioned for 3 min at 0.5 Hz and 1 minute at 1 Hz, before stimulation was stopped for 15 seconds after each stimulation frequency. $Ca^{2+}$ waves and/or spontaneous contractions were detected during the pauses as previously described (Aronsen, J. M., et al., *Hypokalaemia induces Ca(2+) overload and Ca(2+) waves in ventricular myocytes by reducing Na(+),K(+)-ATPase alpha2 activity*. J Physiol, 2015. 593(6): 1509-21). Inclusion criteria were rod-shaped and striated cardiomyocytes and absence of $Ca^{2+}$ waves upon visual inspection 10 seconds prior to electrical stimulation. Cellular arrhythmias were recorded with and without 100 nM Bay 60-7550. In a subset of experiments, cellular arrhythmias were detected with 100 nM Bay 60-7550 with 1 µM TAT-conjugated scrambled peptide or superAKAP. In experiments with peptides, cells were incubated with the peptides for 20 minutes before the start of the protocol.

Whole-Cell $Na^+$ Measurements:

To measure the cytosolic $Na^+$ concentration, isolated rat ventricular myocytes were loaded at room temperature in 10 µM SBFI for 120 min, in the presence of 0.05% Pluronic F-127, followed by 20 minutes of de-esterification. SBFI ratios were detected with a photomultiplier (Photon Technology International, NJ, USA) in myocytes superfused with solution A and field stimulated at 0.5 Hz. Single excitation (340 nm) and dual ratiometric emission (410 nm/590 nm) were used as previously described (Baartscheer, A., C. A. Schumacher, and J. W. Fiolet, *Small changes of cytosolic sodium in rat ventricular myocytes measured with SBFI in emission ratio mode*. J Mol Cell Cardiol, 1997. 29(12): 3375-83). The signal was sampled at 1 Hz and allowed to stabilize before recordings started (typically 10 minutes). 100 nM Bay 60-7550 was applied to study the effect of PDE2 inhibition on cytosolic $Na^+$.

Each cell was calibrated by superfusing the cell with a solution containing 0 and 20 mM $Na^+$. In this range, the SBFI signal was assumed to be linear with the intracellular $Na^+$ levels, as previously described (Despa, S., et al., *Intracellular [Na+] and Na+ pump rate in rat and rabbit ventricular myocytes*. J Physiol, 2002. 539(Pt 1): 133-43). Two different calibration solutions were made, and they were mixed to achieve the desired $Na^+$ concentrations. Both calibration solutions contained (in mM) gramicidin 0.01, ouabain 0.1, Hepes 5, Glucose 5.5, EGTA 2, adjusted to pH 7.2 with TrisBase. Calibration solution with 145 $Na^+$ contained also (in mM): Na-gluconate 115, NaCl 30, KCl 0. Calibration solution with 145 $K^+$ contained (in mM): K-gluconate 115, KCl 30, NaCl 0.

Confocal $Ca^{2+}$ Measurements:

$Ca^{2+}$ sparks were recorded in line-scan mode with a confocal microscope (Zeiss LSM Live7), as described previously (Louch, W. E., et al., *T-tubule disorganization and reduced synchrony of Ca2+ release in murine cardiomyocytes following myocardial infarction*. J Physiol, 2006. 574 (Pt 2): 519-33). In short, a 512 pixel line was drawn longitudinally across the cell and scan time was 1.5 ms. Rat ventricular myocytes were field stimulated at 1 Hz for 3 minutes, before $Ca^{2+}$ sparks were recorded immediately after cessation of stimulation. After a few seconds, 10 mM caffeine was applied to measure the SR $Ca^{2+}$ load. The $Ca^{2+}$ sparks frequency was related to the SR $Ca^{2+}$ load, to prevent load-dependent effects on spark frequency. $Ca^{2+}$ sparks were measured with and without Bay 60-7550 in the same cell. $Ca^{2+}$ sparks were detected and analyzed using SparkMaster in ImageJ (NIH) (Picht, E., et al., *SparkMaster: automated*

*calcium spark analysis with ImageJ.* Am J Physiol Cell Physiol, 2007. 293(3): C1073-81).

In Vivo Recordings of Arrhythmias

Post-banding HF mice, AnkB$^{+/-}$ mice and WT (AnkB$^{+/+}$) mice were anaesthetized in 4% isoflurane, 65% N$_2$O and 31% O$_2$, and ventilated with 2% isoflurane, 66% N$_2$O and 32% O$_2$. Deep surgical anesthesia was confirmed by abolished pain reflexes. Every other mouse was randomized to one of the treatment groups, while the next one was assigned to the other group. Efforts were made to assure that littermate controls were used within one comparison (for instance vehicle vs. Bay 60-7550). One-lead ECG recordings was performed by attaching the mouse limbs to incorporated ECG electrodes on the operating table, which was preheated to 40° C. to maintain a stable body temperature. The ECG was continuously recorded by VEVO2100 software (Visualsonics, Toronto, Canada) during the entire protocol, and the signal was not filtered. A baseline ECG was recorded for 3-5 minute before starting the protocol, and in the rare event of mice having ventricular extrasystoles during this period, they were excluded and the protocol was stopped prior to drug injection. The mice were first injected intraperitoneally (i.p.) with either Bay 60-7550 or vehicle (3 mg/kg) or PF05180999 (1 mg/kg), which was allowed to work for 10 minutes (Vettel, C., et al., *Phosphodiesterase 2 Protects Against Catecholamine-Induced Arrhythmia and Preserves Contractile Function After Myocardial Infarction.* Circ Res, 2017. 120(1): 120-132) before the first injection of caffeine (120 mg/kg i.p.). In experiments with peptides, 5 mM (calculated by assuming free distribution of peptides in the liquid phase of the body, which was assumed to be 0.7 of the total body weight) of TAT-conjugated superAKAP or scrambled peptide were injected i.p. 5 minutes prior to caffeine injection. In experiments with AnkB$^{+/-}$ mice, caffeine was injected i.p. (120 mg/kg i.p.) for a second time 10 minutes after the first injection. The animals were sacrificed by excision of the heart after the end of the protocol, the lung and heart weight were obtained and the left ventricle was transferred to an Eppendorf tube and immediately moved to liquid nitrogen and stored at −80° C. ECG was recorded during the entire protocol. ECG was analyzed using VEVO software.

Preparation of Cardiomyocyte Lysate for Immunoblotting

Non-sterile solution A with 10 mM BDM was pre-heated to 37° C., and plastic wells were coated with 4% laminin in solution A/BDM for 1 hour. Rat ventricular myocytes were isolated as described above, re-suspended in solution A/BDM, plated in the laminin-coated wells and incubated for 1 hour at 37° C. The cells were then gently washed in solution A/BDM, and again incubated for 1 hour at 37° C. Peptides, Isoprenaline or inhibitors were then added as indicated, and allowed to equilibrate for 10 minutes. Finally, cells were harvested in hot (90-100° C.) lysis buffer (1% SDS, 2 mM Na$_3$VO$_4$, 10 mM Tris-HCl, 10 mM NaF, dH$_2$O, pH 7,4), transferred to liquid nitrogen and stored at −80° C.

Immunoprecipitation

Lysates from HEK293 transfected cells were incubated with antibodies for 2 h, thereafter 50 µL protein NG PLUS agarose beads (sc-2003, Santa Cruz Biotechnology) were added overnight at 4° C. Immunocomplexes were washed three times in cold IP-buffer (20 mM HEPES, pH 7.5, 150 mM NaCl, 1 mM EDTA, 1% Triton X-100), centrifuged at 3000 g for 1 min at 4° C., boiled in SDS loading buffer and analysed by immunoblotting. HEK293 cells not transfected with FLAG-PDE2 were used for control.

Immunoblotting

Immunoprecipitates were analysed on 4-15% or 15% SDS-PAGE before blotting onto PVDF membranes. The PVDF membranes and peptide membranes were blocked in 1% casein or 5% milk in TBST for 60 min at room temperature, incubated overnight at 4° C. with primary antibodies, washed three times 10 min in TBS-T and incubated with a HRP-conjugated primary or secondary antibody. Blots were incubated in ECL Prime (GE Healthcare, RPN2232) and chemiluminescence signals were detected by LAS-4000 (Fujifilm, Tokyo, Japan).

Antibodies

Ser68-PLM was a gift from William Fuller. Anti-FLAG and Anti-GFP were used to blot FLAG-PDE2 and GFP-NKA in the immunoprecipitations from HEK293 cells. PDE2 and NKA$_{\alpha 1}$ antibodies were used in proximity ligation assay experiments.

cAMP Measurements

Adult mice ventricular myocytes were transfected with adenovirus type 5 containing GloSensor (Promega, United States) and allowed to incubate for 48 hours before cAMP measurements. The sensor binds cAMP and, when bound to cAMP, emits a light signal that is proportional to cAMP levels.

Nuclear Isolation and Sorting/mRNA Sequencing

Nuclear isolation/sorting and mRNA sequencing were performed as previously described (Thienpont, B., et al., *The H3K9 dimethyltransferases EHMT1/2 protect against pathological cardiac hypertrophy.* J Clin Invest, 2017. 127 (1): 335-348).

Statistics

Data are presented as mean values±S.E. For voltage clamp and field stimulation experiments we used two tailed student's t-test, while Fisher's exact test was employed in all experiments on cellular and in vivo arrhythmias. p<0.05 was considered significant.

Results

PDE2 Regulates NKA Activity

We performed a voltage clamp protocol where the isolated rat ventricular myocytes were exposed to symmetrical concentrations of Na$^+$ (i.e. similar Na$^+$ concentrations in the superfusate and the internal solution) to reduce the unwanted effects of intracellular Na$^+$ gradients. The NKA current was measured as the K$^+$-sensitive current after removal of a saturating concentration of extracellular K$^+$ (from 15 mM to 0 mM [K$^+_e$]) (see FIG. 1A). The NKA current increased in a concentration-response-dependent manner (FIG. 1B), while a high dose of superAKAP, disrupting both PKA-RI and PKA-RII from AKAPs (Gold et al, *Molecular basis of AKAP specificity for PKA regulatory subunits*, Mol. Cell. 2006 Nov. 3; 24(3): 383-95) reduced the NKA current (FIG. 10). This suggests that the NKA activity is regulated by local regulation of cAMP, and that increasing cAMP by inhibiting the cAMP-degrading phosphodiesterases PDE2-4 might increase NKA current, which we next wanted to test.

PDE2 inhibition with three different pharmacological inhibitors (EHNA, PF05180999 and Bay 60-7550) robustly increased the NKA current (FIG. 2A), while neither PDE3 inhibition with Cilostamide or PDE4 inhibition with Rolipram had any detectable effects (FIG. 2C). We also found increased NKA current in a PDE2-deficient mice model (FIG. 2B) further strengthening the finding of PDE2 regulating NKA activity.

In line with the functional recordings, we also found increased phosphorylation of phospholemman (PLM) at its main site for PKA phosphorylations, serine 68, after inhibition of PDE2. We also found increased PLM ser-68 phosphorylation with PDE4 inhibition, while there was no effect of PDE3 inhibition (FIG. 2D).

PDE2 and NKA Colocalize and Interact

PDE2 appears to be the main cAMP-PDE regulating NKA activity. If PDE2 regulates NKA through a local regulatory effect, then this interaction could be targeted specifically for therapeutically purposes. To investigate whether PDE2 and NKA reside in the same intracellular compartment, we performed a proximity ligation assay (Duolink®) which is used to detect intracellular colocalization between proteins with 30-40 nm resolution (Soderberg, O., et al., *Direct observation of individual endogenous protein complexes in situ by proximity ligation*. Nat Methods, 2006. 3(12): 995-1000). The light dots in FIG. 3A (image to the right) suggest colocalization in intact rat ventricular myocytes between PDE2 and NKA, while the other images are negative controls. FIG. 3B shows a quantification of the light dots, with the three bars to the right showing much higher levels of light dots when both NKA and PDE2 antibodies were present. We then co-expressed FLAG-tagged PDE2 and GFP-tagged NKA or GFP-NKA alone in HEK293 cells, and immunoprecipitated FLAG. The levels of GFP-tagged NKA was higher when co-expressed with FLAG-PDE2, showing that PDE2 and NKA co-immunoprecipitates (FIG. 3C). These results indicate that PDE2 and NKA co-localizes in cells, providing a structural basis for the proposed local regulation of NKA activity by PDE2.

PDE2 Inhibition Reduces $Ca^{2+}$ Transient Amplitude and SR $Ca^{2+}$ Load

Having shown that PDE2 regulates NKA activity and colocalizes with NKA, we next wanted to investigate whether PDE2 influenced the $Ca^{2+}$ homeostasis in ventricular myocytes. First, we measured $Ca^{2+}$ transients in Fluo4-AM-loaded, field-stimulated rat ventricular myocytes, and we observed a decrease in $Ca^{2+}$ transient amplitude without alterations on the $Ca^{2+}$ extrusion rate (FIG. 4A-B) after application of Bay 60-7550. SR $Ca^{2+}$ load was measured with rapid pulses of caffeine (FIG. 4C), and we found reduced SR $Ca^{2+}$ load after PDE2 inhibition (FIG. 4A, right panel), in accordance with the observed reduction in $Ca^{2+}$ transient amplitude. We also performed the same experiments in isolated ventricular myocytes from PDE2KO mice, and we found similar results with reduced $Ca^{2+}$ transient amplitude and SR $Ca^{2+}$ load with no effect on the $Ca^{2+}$ extrusion rate (FIG. 4D).

PDE2 Inhibition Increases NCX-Mediated $Ca^{2+}$ Extrusion

A reduction in $Ca^{2+}$ transient amplitude and SR $Ca^{2+}$ load after PDE2 inhibition could be explained by altered activity in the main $Ca^{2+}$ handling proteins in the ventricular myocyte, i.e. L-type $Ca^{2+}$ channel, RyR, NCX, SERCA or non-SERCA/non-NCX $Ca^{2+}$ extruding proteins (PMCA and mitochondrial uniporter). To elucidate the role of the various $Ca^{2+}$ handling proteins in the $Ca^{2+}$ homeostasis following PDE2 inhibition, we did a series of experiments where we measured their activity after application of Bay 60-7550. We did not find any effect on SERCA function or the non-SERCA/non-NCX activity in rat ventricular myocytes after PDE2 inhibition, while the $Ca^{2+}$ extrusion through NCX was significantly increased (FIG. 5A-B). This same pattern was also found in experiments conducted in PDE2KO mice, with increased $Ca^{2+}$ extrusion through NCX and unaltered activity of SERCA and non-SERCA/non-NCX $Ca^{2+}$ handling proteins (FIG. 5C). Altered NKA activity could affect NCX activity through alterations in local or global $Na^+$ (Despa, S., J. B. Lingrel, and D. M. Bers, *Na(+)/K(+)-ATPase alpha2-isoform preferentially modulates Ca2(+) transients and sarcoplasmic reticulum Ca2(+) release in cardiac myocytes*. Cardiovasc Res, 2012. 95(4): 480-6), but we were not able to detect any differences in global intracellular $Na^+$ using SBFI (FIG. 5D), suggesting that local $Na^+$ gradients are involved.

In voltage clamped rat ventricular myocytes, we did not find any effect of PDE2 inhibition on the L-type $Ca^{2+}$ current (FIG. 6A-B) or $Na^+$ current (FIG. 6E). We also measured $Ca^{2+}$ sparks in Fluo4-AM-loaded rat ventricular myocytes using line-scan mode on a confocal microscopy, and this revealed no difference in the $Ca^{2+}$ sparks frequency between control and PDE2 inhibition, suggesting unaltered RyR activity (FIG. 6C-D).

PDE2 inhibition thus leads to increased NKA current, increased $Ca^{2+}$ extrusion through NCX and reduced $Ca^{2+}$ transient amplitude and SR $Ca^{2+}$ load, and these results harmonize with the following reasoning: 1) Increased NKA activity leads to reduced local intracellular $Na^+$, 2) and the reduced intracellular $Na^+$ increases the driving force for $Ca^{2+}$ efflux through NCX, meaning that more $Ca^{2+}$ is extruded through NCX out of the myocyte, 3) Finally, more sarcolemmal $Ca^{2+}$ extrusion through NCX means that less $Ca^{2+}$ is available for intracellular $Ca^{2+}$ cycling through SERCA, with the net effect being that $Ca^{2+}$ is removed out of the cell, giving a smaller $Ca^{2+}$ transient and a smaller SR $Ca^{2+}$ load.

PDE2 Inhibition Prevents Cellular Tachycardias $Ca^{2+}$ overloading is a well-established cause of arrhythmias (Pogwizd, S. M. and D. M. Bers, *Cellular basis of triggered arrhythmias in heart failure*. Trends Cardiovasc Med, 2004. 14(2): 61-6; and Kranias, E. G. and D. M. Bers, *Calcium and cardiomyopathies*. Subcell Biochem, 2007. 45: 523-37) leading to $Ca^{2+}$ waves (Aronsen, J. M., et al., *Hypokalaemia induces Ca(2+) overload and Ca(2+) waves in ventricular myocytes by reducing Na(+),K(+)-ATPase alpha2 activity*. J Physiol, 2015. 593(6): 1509-21) and deleterious secondary effects (Pezhouman, A., et al., *Molecular Basis of Hypokalemia-Induced Ventricular Fibrillation*. Circulation, 2015. 132(16): 1528-1537), and conversely, agents that reduces intracellular $Ca^{2+}$, such as $Ca^{2+}$ channel blockers, might protect against arrhythmias. Heart failure is a disease with a huge risk of ventricular arrhythmias (Pogwizd, S. M. and D. M. Bers, *Cellular basis of triggered arrhythmias in heart failure*. Trends Cardiovasc Med, 2004. 14(2): 61-6), while Ankyrin B syndrome is a genetic disease which causes type 4 long-QT syndrome (Mohler, P. J., et al., *Ankyrin-B mutation causes type 4 long-QT cardiac arrhythmia and sudden cardiac death*. Nature, 2003. 421(6923): 634-9). Since PDE2 inhibition reduced $Ca^{2+}$ transient amplitude, we hypothesized that PDE2 inhibition would prevent $Ca^{2+}$ waves in ventricular myocytes from heart failure mice and Ankyrin $B^{+/-}$ mice (long QT syndrome). First, we confirmed that PDE2 inhibition increased NKA currents and reduced $Ca^{2+}$ transients in ventricular myocytes from post-banding mice with heart failure (FIG. 7A-B). We detected a considerable amount of $Ca^{2+}$ waves in myocytes both from heart failure mice and Ankyrin $B^{+/-}$ mice (long QT syndrome), but the $Ca^{2+}$ waves were largely reduced or abolished with PDE2 inhibition (FIG. 7C-D). In WT mice (Ankyrin $B^{+/-}$ mice littermates), there was no difference in the $Ca^{2+}$ wave frequency, which is as expected considering the low frequency of $Ca^{2+}$ waves during control conditions (FIG. 7D, right panel).

In conclusion, PDE2 inhibition prevents cellular tachycardias in known models of cardiac arrhythmias.

PDE2 Inhibition Prevents Ventricular Tachycardia in Mice with Heart Failure and Ankyrin B$^{+/-}$ Syndrome (Long QT Syndrome)

To test whether PDE2 inhibition protects against ventricular tachycardias in vivo, we performed a protocol where we acutely injected anesthetized post-banding HF mice and AnkB$^{+/-}$ mice with 120 mg/kg caffeine (Kannankeril, P. J., et al., *Mice with the R176Q cardiac ryanodine receptor mutation exhibit catecholamine-induced ventricular tachycardia and cardiomyopathy*. Proc Natl Acad Sci USA, 2006. 103(32): 12179-84) and monitored the heart rhythm with a one-lead ECG (protocols outlined in FIG. 8A and 9A). The protocol was also tested in WT animals, where one caffeine injection was not sufficient to elicit arrhythmias (data not shown), while both post-banding HF mice and AnkB$^{+/-}$ mice exhibited ventricular arrhythmias. Examples of a normal sinus rhythm and ventricular tachycardia are shown in FIG. 8B, and the typical ventricular tachycardias that we observed were bidirectional ventricular tachycardias and multifocal ventricular tachycardias. In experiments with Bay 60-7550, 4 out of 5 (80%) of the heart failure mice that received vehicle injection (control) developed ventricular tachycardia and cardiac arrest, while this outcome was seen in 0 out of 5 (0%) of the heart failure mice that received an injection with 3 mg/kg Bay 60-7550 (Vettel, C., et al., *Phosphodiesterase 2 Protects Against Catecholamine-Induced Arrhythmia and Preserves Contractile Function After Myocardial Infarction*. Circ Res, 2017. 120(1): 120-132) (FIG. 8C). 1 mouse in the Bay 60-7550 group developed ventricular arrhythmias, but this did notably not develop into cardiac arrest. In experiments with PF05180999, 4 out of 5 (80%) of the heart failure mice that received vehicle injection (control) developed ventricular tachycardia, while this was seen in only 1 out of 5 (20%) of the heart failure mice that received an injection with 1 mg/kg PF05180999 (FIG. 8D).

In the experiments with Bay 60-7550 on Ankyrin B$^{+/-}$ mice (long QT syndrome), 5 out of 8 (63%) in the control group (vehicle injection) developed ventricular tachycardia (FIG. 8D). In addition, 2 mice developed supraventricular tachycardia (data not shown). In contrast, 0 out of 8 (0%) in the intervention group (Bay 60-7550 injection) developed ventricular tachycardia (FIG. 9C) or supraventricular tachycardia (data not shown). In the experiments with PF05180999, 5 out of 5 (100%) developed ventricular tachycardia in the control group (vehicle injection), while 1 out of 5 (20%) developed ventricular tachycardia with 1 mg/kg PF05180999 (FIG. 9D).

QT prolongation is a known risk factor for ventricular tachycardias (Osadchii, O. E., *Impact of hypokalemia on electromechanical window, excitation wavelength and repolarization gradients in guinea-pig and rabbit hearts*. PLoS One, 2014. 9(8): e105599). We observed an increased QT interval from baseline ECG to post-caffeine injection in the vehicle group in both post-banding HF and AnkB$^{+/-}$ mice, while there was no difference in the QT interval in the Bay 60-7550 and PF05180999 groups (FIGS. 8C-D and 9C-D, right panels).

In summary, we find that PDE2 inhibition prevents deleterious ventricular tachycardias and QT prolongation in established mice models of cardiac arrhythmias. This indicates that PDE2 inhibition is a novel target for treatment of cardiac tachycardias in a variety of clinical settings, for instance in heart failure patients.

PDE2 Regulation of NKA is Dependent on Local PKA-RII Activity

Since PDE2 and NKA colocalize in intact ventricular myocytes, an intriguing possibility is that PDE2 regulation of NKA is dependent on local cAMP gradients and local PKA activity. In line with this idea, we did not detect any global increase or decrease in cAMP levels after treatment with Bay 60-7550. We used Isoprenaline as a positive control, and application of 20 nM Isoprenaline largely increased cAMP levels (FIG. 10A). Low doses of RIAD and superAKAP (1 µM) are established, highly specific disruptors of AKAP-bound PKA-RI (RIAD) and PKA-RII (superAKAP), while a higher concentration of superAKAP (20 µM) disrupts both PKA-RI and PKA-RII (Gold et al, *Molecular basis of AKAP specificity for PKA regulatory subunits*, Mol. Cell. 2006 Nov. 3; 24(3): 383-95). Following dialysis of superAKAP (both high and low dose) into the voltage clamped myocytes, PDE2 inhibition did not alter NKA current. However, PDE2 inhibition still increased the NKA current in the presence of RIAD (PKA-RI disruptor), suggesting that PDE2 regulation of NKA is exclusively dependent on AKAP-bound, local PKA-RII activity, not PKA-RI (FIG. 10C). We also found positive co-IP between NKAα2 and both the catalytic site on PKA and PKA RIIα (FIG. 10B), which supports the idea of a local, regulatory complex consisting of NKA, PDE2 and an AKAP-bound PKA-RII (see FIG. 12 for proposed model).

The Anti-Arrhythmic Effect of PDE2 Inhibition is Dependent on AKAP-Bound PKA-RII We propose that PDE2 inhibition activates NKA through regulation of local cAMP pools and prevents ventricular arrhythmias, so we hypothesized that both the cellular and in vivo arrhythmias that were prevented with PDE2 inhibition would reappear after application of superAKAP. As shown in FIG. 10C, there is an increased frequency of Ca$^{2+}$ waves with Bay 60-7550 present when cells were incubated and superfused with TAT-superAKAP compared to TAT-scrambled peptide. The increased amount of Ca$^{2+}$ waves was seen both in post-banding HF and AnkB$^{+/-}$, and at both frequencies tested (FIG. 10D).

We also tested the ability of superAKAP to reverse the anti-arrhythmic effect of PDE2 inhibition in vivo as outlined in FIG. 11A. Both in post-banding HF mice (4 out of 6) and in AnkB$^{+/-}$ mice (3 out of 5) did ventricular arrhythmias appear during Bay 60-7550 treatment when the mice were injected with TAT-superAKAP. However, there were no observed arrhythmias in post-banding HF mice (0 out of 6) and in AnkB$^{+/-}$ mice (0 out of 5) during Bay 60-7550 treatment when the mice were injected with TAT-scramble. These results confirm that PDE2 inhibition prevents cellular and in vivo tachycardias through regulation of a local signaling domain that activates NKA.

PDE2 is Up-Regulated in Cardiomyocytes in Human Hypertrophy and Ageing

In order for PDE2 inhibition to be a future anti-arrhythmic treatment option, it needs to be established that PDE2 is present in human cardiac tissue and in disease. Although it previously has been reported that PDE2 is up-regulated in human heart failure (Mehel, H., et al., *Phosphodiesterase-2 is up-regulated in human failing hearts and blunts beta-adrenergic responses in cardiomyocytes*. J Am Coll Cardiol, 2013. 62(17): 1596-606), these analysis were performed on left ventricular tissue, which also contains other cell types (Thienpont, B., et al., *The H3K9 dimethyltransferases EHMT1/2 protect against pathological cardiac hypertrophy*. J Clin Invest, 2017. 127(1): 335-348). We did mRNA sequencing on isolated and sorted cardiomyocyte nuclei, and find that PDE2A-mRNA expression is up-regulated in human left ventricular hypertrophy and in elderly individuals. PDE2A-mRNA expression was also increased in cardiomyocyte nuclei from rats with post-banding HF (FIG. 13). Thus, it is found that PDE2A is up-regulated in cardiomyocytes in relevant disease models, meaning that PDE2A can be targeted for anti-arrhythmic purposes in humans.

Conclusion:

We have shown that PDE2 inhibition strongly prevents ventricular tachycardias in post-banding HF mice and heterozygous Ankyrin B$^{+/-}$ mice (long QT syndrome) through a novel anti-arrhythmic mechanism, where PDE2 inhibition increases NKA activity through regulation of local PKA activity, ultimately leading to reduced Ca$^{2+}$ loading of the myocytes and reduced cellular and in vivo arrhythmogenecity. Ca$^{2+}$ extrusion through NCX was increased after PDE2 inhibition, offering a mechanism for the reduced Ca$^{2+}$ loading of the myocytes, whereas no other Ca$^{2+}$ handling proteins was regulated by PDE2 inhibition in our hands, including LTCC, RyR, SERCA2 and non-SERCA2-non-NCX Ca$^{2+}$ extruding proteins. The increased Ca$^{2+}$ extrusion through NCX could either be explained by a direct PDE2-mediated effect on NCX or downstream to alterations in intracellular Na$^+$. It has previously been shown that activation of beta-adrenergic signaling and subsequent phosphorylation of PLM regulates NCX negatively (Cheung, J. Y., et al., *Regulation of cardiac Na+/Ca2+ exchanger by phospholemman*. Ann NY Acad Sci, 2007. 1099: 119-34; and Wanichawan, P., et al., *Development of a high-affinity peptide that prevents phospholemman (PLM) inhibition of the sodium/calcium exchanger 1 (NCX1)*. Biochem J, 2016. 473(15): 2413-23). Thus, it is unlikely that PDE2 inhibition would increase Ca$^{2+}$ extrusion through NCX through an effect on PLM. NKA activation leads to reduced intracellular Na$^+$, which could have downstream effects on NCX, as shown previously by our group and others (Aronsen, J. M., et al., *Hypokalaemia induces Ca(2+) overload and Ca(2+) waves in ventricular myocytes by reducing Na(+),K(+)-ATPase alpha2 activity*. J Physiol, 2015. 593(6): 1509-21; and Despa, S., J. B. Lingrel, and D. M. Bers, *Na(+)/K)+)-ATPase alpha2-isoform preferentially modulates Ca2(+) transients and sarcoplasmic reticulum Ca2(+) release in cardiac myocytes*. Cardiovasc Res, 2012. 95(4): 480-6). NKA and NCX have been shown to interact in a local Na$^+$ domain, where downstream effects on Ca$^{2+}$ homeostasis and contractility are poorly predicted by changes in global intracellular Na$^+$ (Despa, S., J. B. Lingrel, and D. M. Bers, *Na(+)/K)+)-ATPase alpha2-isoform preferentially modulates Ca2(+) transients and sarcoplasmic reticulum Ca2(+) release in cardiac myocytes*. Cardiovasc Res, 2012. 95(4): 480-6). In the present study, we did not find global changes in intracellular Na$^+$, although the sensitivity of intracellular Na$^+$ measurements using SBFI is low (Baartscheer, A., C. A. Schumacher, and J. W. Fiolet, *Small changes of cytosolic sodium in rat ventricular myocytes measured with SBFI in emission ratio mode*. J Mol Cell Cardiol, 1997. 29(12): 3375-83; and Swift, F., et al., *The Na+/K+-ATPase alpha2-isoform regulates cardiac contractility in rat cardiomyocytes*. Cardiovasc Res, 2007. 75(1): 109-17), suggesting that the observed effect on NCX is due to NKA regulation of local Na$^+$ pools in a restricted domain.

Reduced NKA activity is an emerging pro-arrhythmic pathway, evident by the classical digitalis-induced arrhythmias, but reduced NKA activity has also been highlighted more recently, by our group (Aronsen, J. M., et al., *Hypokalaemia induces Ca(2+) overload and Ca(2+) waves in ventricular myocytes by reducing Na(+),K(+)-ATPase alpha2 activity*. J Physiol, 2015. 593(6): 1509-21) and Pezhouman et al. (Pezhouman, A., et al., *Molecular Basis of Hypokalemia-Induced Ventricular Fibrillation*. Circulation, 2015. 132(16): 1528-1537) to have a role in hypokalemia-induced arrhythmias (Faggioni, M. and B. C. Knollmann, *Arrhythmia Protection in Hypokalemia: A Novel Role of Ca2+-Activated K+ Currents in the Ventricle*. Circulation, 2015. 132(15): 1371-3). Although this implies that increased NKA activity could have an anti-arrhythmic effect, no such NKA activators exist, leaving this opportunity unexplored. We report here that PDE2 inhibition increases NKA activity with 30-50%. We and others have previously reported that a similar reduction in NKA activity has strong pro-arrhythmic effects. It has also been shown previously that small changes in total NKA activity could translate into large downstream effects in contractility (Despa, S., J. B. Lingrel, and D. M. Bers, *Na(+)/K)+)-ATPase alpha2-isoform preferentially modulates Ca2(+) transients and sarcoplasmic reticulum Ca2(+) release in cardiac myocytes*. Cardiovasc Res, 2012. 95(4): 480-6), depending on NKA isoform and co-localization with NCX.

A previous study found that overexpression of PDE2 protects against catecholamine-induced arrhythmias (Vettel, C., et al., *Phosphodiesterase 2 Protects Against Catecholamine-Induced Arrhythmia and Preserves Contractile Function After Myocardial Infarction*. Circ Res, 2017. 120(1): 120-132), which apparently contrasts with our findings. PDE2 is a dual-specific PDE, degrading both cGMP and cAMP, but with different affinities and maximal velocity rate (Bender, A. T. and J. A. Beavo, *Cyclic nucleotide phosphodiesterases: molecular regulation to clinical use*. Pharmacol Rev, 2006. 58(3): 488-520). Importantly, PDE2 activity has been shown to be highly compartmentalized, regulating cAMP levels in specific domains, suggesting that PDE2 could have a highly differentiated role in various domains (Zaccolo, M. and M. A. Movsesian, *cAMP and cGMP signaling cross-talk: role of phosphodiesterases and implications for cardiac pathophysiology*. Circ Res, 2007. 100(11): 1569-78). Following catecholamine-induced activation of beta-adrenergic receptors, overexpression of PDE2 is expected to limit the intracellular rise in cAMP (Vettel, C., et al., *Phosphodiesterase 2 Protects Against Catecholamine-Induced Arrhythmia and Preserves Contractile Function After Myocardial Infarction*. Circ Res, 2017. 120(1): 120-132). However, it is not clear whether cAMP is altered in specific compartments or whether the observed beneficial effect is due to a global reduction in cAMP levels. In the present study, we report that PDE2 inhibition increases NKA current, reduces intracellular Ca$^{2+}$ loading and prevents cellular and in vivo tachycardias without prior activation of the beta-adrenergic receptors. We find no global increase (or decrease) in cAMP levels after PDE2 inhibition without activation of beta-adrenergic receptors, suggesting that PDE2 inhibition is beneficial by regulating cAMP levels specific domains. We propose that PDE2 inhibition specifically activates NKA with few or no other effects on Ca$^{2+}$ handling proteins. Our approach differs from the previous study in two important areas: 1) Activation of beta-adrenergic receptors leads to a global increase in intracellular cAMP; 2) The overexpression of PDE2 does not necessarily alter cAMP in specific domains, but might reflect a general, global reduction in cAMP levels. A previous study found beneficial effects on cardiac hypertrophy after PDE2 inhibition, but the effect was abrogated after disruption of local PKA activity (Zoccarato, A., et al., *Cardiac Hypertrophy Is Inhibited by a Local Pool of cAMP Regulated by Phosphodiesterase 2*. Circ Res, 2015. 117(8): 707-19). Together with our findings in the present study, this suggests that PDE2 inhibition is beneficial due to increase of cAMP in specific domains, while the proposed beneficial effect of PDE2 overexpression might be due to an unspecific effect with global cAMP degradation.

Example 2

The methods of Example 1 were repeated with other known PDE2 inhibitors to demonstrate their activity in the prevention of ventricular tachycardias in mice.

In Vivo Recordings of Arrhythmias

ND-7001 (10 mg/kg) and LuAF64280 (20 mg/kg), were tested in HF mice 1 week after AB using the same experimental set-up as described in Example 1. DMSO was used for control injections. Marked cardiac remodeling was verified in all mice before injection of the PDE2 inhibitor and subsequent caffeine.

Results

PDE2 Inhibition Prevents Ventricular Tachycardia in Mice with Heart Failure

Both ND-7001 and LuAF64280 protected against VTs in HF mice: ND-7001 0/5 (0%) developed VT; LuAF64280 0/3 (0%) developed VT (FIG. 14). In total, four PDE2 inhibitors, Bay 60-7550, PF05180999, ND-7001, and LuAF64280, protected against VT in HF mice.

Conclusion

It has been shown that two further PDE2 inhibitors prevent ventricular tachycardia in established models.

Example 3

The anti-arrhythmic effect of the PDE2 inhibitor Bay 60-7550 was tested against Metoprolol and in combination with Metoprolol, a commonly used anti-arrhythmic drug.

In Vivo Recordings of Arrhythmias

The anti-arrhythmic effect of the PDE2 inhibitor Bay 60-7550 was tested against Metoprolol in the same way as described in Example 1. We also included groups that received control injections and the combination of Bay 60-7550 and Metoprolol. Mice were randomly assigned to treatment groups, but with pre-determined group sizes. All groups were treated for five days; 5.5 mg/kg Metoprolol (see Zhou, Q., et al., *Carvedilol and its new analogs suppress arrhythmogenic store overload-induced Ca2+ release*. Nat. Med. 2011. 17(8): 1003-9) was injected once every day (in the morning), while 3 mg/kg Bay 60-7550 and control were injected twice every day (morning and evening). For chronic injections Bay 60-7550 was dissolved in 5% ethanol and 95% sunflower oil, and the control group received the same vehicle. 5% ethanol was added to the injection in the Metoprolol-only group to minimize ethanol-dependent effects. On the fifth day, we recorded baseline ECGs of all the animals before receiving their final injection. The final injections were given 10-20 min prior to the arrhythmia protocol. Final injections, anesthesia, arrhythmia provocation, ECG recordings and ECG analysis were performed as described in Example 1.

Results

PDE2 Inhibition is Superior to Beta-Blockers in Preventing $Ca^{2+}$-Induced Ventricular Arrhythmias Clinically, beta-blockers are the most commonly used anti-arrhythmic drug to prevent ventricular tachyarrhythmias, both in HF and in genetic arrhythmia syndromes (see Al-Khatib, S. M., et al., 2017 *AHA/ACC/HRS Guideline for Management of Patients With Ventricular Arrhythmias and the Prevention of Sudden Cardiac Death: A Report of the American College of Cardiology/American Heart Association Task Force on Clinical Practice Guidelines and the Heart Rhythm Society*. Circulation, 2017). The anti-arrhythmic mechanism of action is mainly to block cAMP/PKA-dependent effects downstream of β-adrenergic receptors, while we propose that the anti-arrhythmic effect of PDE2 inhibition is due to specific activation of NKA and reduction in intracellular Ca2+ levels. We investigated the following questions: First, is PDE2 inhibition superior to beta-blockers in preventing Ca2+-induced ventricular arrhythmias? Second, is the anti-arrhythmic effect of PDE2 inhibition still present when combined with beta-blockers? To answer these questions, we randomized 55 AnkB+/− mice into four groups; vehicle, Metoprolol (5.5 mg/kg), Bay 60-7550 (3 mg/kg), or the combination of Bay 60-7550 (3 mg/kg) and Metoprolol (5.5 mg/kg). All mice received injections for five days, and on the final day, the mice were injected with caffeine (120 mg/kg) to induce ventricular arrhythmias (FIG. 15A). In the vehicle group, 8/11 developed VT and 11/11 developed ventricular arrhythmias (VT, ventricular bigemini, or coupled ventricular extrasystoles (VES)). In the Metoprolol group, 5/15 developed VT and 14/15 developed ventricular arrhythmias (VT, ventricular bigemini, and coupled VES). In contrast, the mice treated with Bay 60-7550 had significantly fewer ventricular arrhythmias (4/13, VT and ventricular bigemini), while 2/13 developed VT. In the group that received the combination of Metoprolol and Bay 60-7550, there were 0/15 mice with VT and 2/15 with ventricular arrhythmias (ventricular bigemini) (FIG. 15B and C). There was a QT prolongation following Metoprolol injection in both Metoprolol alone and in combination with Bay 60-7550. Neither of the groups that received Bay 60-7550 developed QT prolongation after caffeine injection, in contrast to Metoprolol and vehicle groups (FIG. 15D).

Beta-blockers constitute a cornerstone in modern anti-arrhythmic treatment, but our results suggest that PDE2 inhibition can complement and even provide an additive effect to this regime.

Conclusion

The results clearly suggest that PDE2 inhibition alone or in combination with Metoprolol prevented $Ca^{2+}$-induced ventricular arrhythmias more efficiently than the control or Metoprolol alone. Many cardiac patients already use a beta-blocker, so it is an important finding that the combination of PDE2 inhibitors and beta-blockers is superior to the beta-blocker alone. This suggests that PDE2 inhibition is effective as an add-on therapy, which could be highly relevant in several clinical settings.

Example 4

In an extension to the experiments in Example 1, $Ca^{2+}$ currents, $Na^+$ currents, $K^+$ currents and action potentials (APs) were also investigated in respect of BAY 60-7550.

L-Type $Ca^{2+}$ Currents (LTCC)

Wide tipped patch pipettes (1.4-1.8 MΩ) were filled with internal solution (in mM, modified from Leroy, J. et al., *Phosphodiesterase 4B in the cardiac L-type Ca(2)(+) channel complex regulates Ca(2)(+) current and protects against ventricular arrhythmias in mice*. J. Clin. Invest. 2011. 121 (7): 2651-61): CsCl 122, HEPES 10, MgATP 5, $MgCl_2$ 0.7 (free $Mg^{2+}$ 0.6 mM), $Na_2$Phosphodicreatinine 5, EGTA 10, $CaCl_2$ 0.2 (free $Ca^{2+}$ 3 nM), cAMP 0.005, pH 7.2 with CsOH. Series resistance was between 4-8 MΩ in all recordings. 100 ms voltage steps were performed from a holding potential of −45 mV to various test potentials in the range −45 mV to 55 mV (10 mV) steps.

Na$^+$ Currents

Low resistance pipettes (1.4-2.5 MΩ) were filled with internal solution (in mM, modified from Leroy, J. et al., *Phosphodiesterase 4B in the cardiac L-type Ca(2)(+) channel complex regulates Ca(2)(+) current and protects against ventricular arrhythmias in mice*. J. Clin. Invest. 2011. 121 (7): 2651-61): CsCl 122, HEPES 10, MgATP 5, MgCl$_2$ 0.7 (free Mg$^{2+}$ 0.6 mM), Na$_2$Phosphodicreatinine 5, EGTA 10, CaCl$_2$ 0.2 (free Ca$^{2+}$ 3 nM), cAMP 0.005, pH 7.2 with CsOH. Series resistance was between 4-7.5 MΩ in all recordings. The cells were patched in solution A, but after whole-cell access was reached, solution D was applied (in mM): N-metyl-D-glucamine 125, NaCl 10, CsCl 5, D-glucose 5, MgCl$_2$ 1.2, HEPES 10, NiCl$_2$ 5, pH 7.4 with CsOH. 20 μM Nifedipine was added on experiment day to inhibit L-type Ca$^{2+}$ channels. Holding potential was −80 mV. 50 ms voltage steps were performed from a holding potential of −80 mV to various test potentials in the range −80 mV to 70 mV (15 mV) steps.

Background K$^+$ Currents

K$^+$ currents were measured as described previously (see Aronsen, J. M. et al., *Hypokalaemia induces Ca(2+) overload and Ca(2+) waves in ventricular myocytes by reducing Na(+),K(+)-ATPase alpha2 activity*. J. Physiol, 2015. 593 (6): 1509-21). Briefly, 500 ms voltage steps were performed from a holding potential of −80 mV to various test potentials in the range −170 mV to 50 mV (10 mV) steps. Currents were analyzed at the stable phase towards the end of the pulse. Control recordings and recordings with Bay 60-7550 were performed in the same cells. Pipette resistance was 2-2.5 MΩ with a series resistance of 4-8 MΩ.

Action Potentials (APs)

APs were triggered by a 3-ms suprathreshold current injection. Pipette solution contained (in mM): KCl 130, NaCl 10, HEPES 10, MgATP 5, MgCl$_2$ 1, EGTA 0.5, cAMP 0.005, pH adjusted to 7.2 with KOH. The cells were superfused with solution A. Pipette resistance was 2-2.5 MΩ with a series resistance of 4.8-9.3 MΩ. APs were analyzed at 20% (APD20), 50% (APD50), 70% (APD70) and 90% (APD90), where 0% is the peak potential and 100% is the resting membrane potential, and at a given relative potential, the actual membrane potential was measured. Control recordings and recordings with Bay 60-7550 were performed in the same cells.

Results

PDE2 Inhibition has High Target Specificity

Current anti-arrhythmic treatments may be divided into class 1-4 anti-arrhythmics, including inhibitors of Na$^+$, K$^+$, and Ca$^{2+}$ channels. In FIG. 16c, we showed that PDE2 inhibition had no effect on Ca$^{2+}$ currents. Here we also found that PDE2 inhibition had no effect on Ca$^{2+}$ currents (FIG. 17a), K$^+$ currents (FIG. 17b), or Na$^+$ currents (FIG. 17c) in voltage clamped ARVMs. Inhibition of Na$^+$, K$^+$, and Ca$^{2+}$ current is expected to increase action potential duration (APD). In contrast, we observed that PDE2 inhibition shortened the AP at APD50, APD70, and APD90 (FIG. 17d), consistent with the model that PDE2 inhibition selectively increases NKA activity without affecting Na$^+$, K$^+$, and Ca$^{2+}$ currents. These results show that PDE2 inhibition activates NKA with high specificity, with no effects on other, previously known anti-arrhythmic targets.

Conclusion

Current pharmacological treatment strategies for ventricular arrhythmias include class I-IV anti-arrhythmic drugs. However, some anti-arrhythmic drugs are contraindicated in patients with structural heart disease due to its pro-arrhythmic effects. New anti-arrhythmic strategies should preferably target specific arrhythmia mechanisms without too many off-target effects. Our results suggest that PDE2 inhibitors activates NKA with no effects on Ca$^{2+}$ handling proteins and ion channels, including SERCA, RyR, non-SERCA-non-RyR Ca$^{2+}$ extrusion proteins, Ca$^{2+}$ current, Na$^+$ current and K$^+$ currents (inward rectifier and delayed rectifiers). We believe that this high level of specificity derives from the close interaction between NKA and PDE2.

By using a wide variety of molecular biology and imaging techniques, we show that NKA and PDE2 interacts and co-localizes in cardiomyocytes, and that PDE2 inhibition increases cAMP locally around NKA with no global increase in cAMP. Further, PDE2 regulation of NKA is blunted in the presence of superAKAP, a peptide that with high specificity displaces the RII-PKA from AKAPs. In line with this, PDE2 inhibition does not prevent VT in heart failure or AnkB$^{+/−}$ in the presence of superAKAP, showing that the anti-arrhythmic effect is dependent on local cAMP domains. Thus, PDE2 inhibition as an anti-arrhythmic treatment represents a novel treatment strategy in two ways: 1) As an activator of NKA and 2) by targeting cAMP levels in discrete domains.

Example 5

In Vivo Recordings of Arrhythmias

CPVT mice were bred as previously described (Lehnart S E et al., *Leaky Ca2+ release channel/ryanodine receptor 2 causes seizures and sudden cardiac death in mice*, Journal of Clinical Investigation 2008 June 118(6): 2230-45). Bay 60-7550 (3 mg/kg) was tested in CPVT mice. To induce ventricular tachycardia, the mice were injected with 60 mg/kg caffeine and 50 ng/kg Isoprenaline. 50% Ethanol was used for control injections.

Results

PDE2 Inhibition Prevents Ventricular Tachycardia in Mice with CPVT

Bay 60-7550 protected against VTs in CPVT mice: Bay 60-7550 2/7 (28%) developed VT; compared to 100% of controls (6/6) (FIG. 18). In total, PDE2 inhibition prevents ventricular tachycardias in three different mice models, HF, Ankyrin B$^{+/−}$ (long QT syndrome), and CPVT.

Conclusion

It has been shown that PDE2 inhibition protects against an additional cardiac disease with increased risk of ventricular tachycardias.

The invention claimed is:

1. A method of treatment of ventricular tachycardia in a subject in need thereof, the method comprising the step of administering to the subject a compound which is a selective PDE2 inhibitor.

2. The method of claim 1, wherein said compound has a selectivity for inhibiting the activity of PDE2 which is at least 10-fold compared to at least one other PDE type.

3. The method of claim 2, wherein said compound has a selectivity for inhibiting the activity of PDE2 which is at least 10-fold compared to all other PDE types.

4. The method of claim 2, wherein said selectivity is at least 20-fold.

5. The method of claim 1, wherein said compound inhibits PDE2 with an IC$_{50}$ value of less than about 100 nM.

6. The method of claim 1, wherein said compound is selected from any of the following, their pharmaceutically acceptable salts or prodrugs thereof:

| Compound | Name |
|---|---|
| 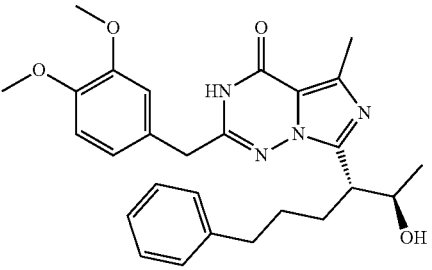 [SMILES: COc1ccc(Cc2nn3c([C@@H](CCCc4ccccc4)[C@@H](C)O)nc(C)c3c(=O)[nH]2)cc1OC] | BAY 60-7550 2-(3,4-dimethoxy)benzyl)-7-[(2R,3R)-2-hydroxy-6-phenylhexan-3-yl]-5-methylimidazo[5,1-f][1,2,4]triazin-4(3H)-one |
| 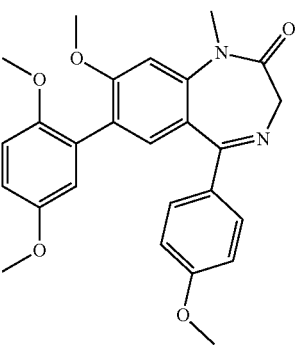 [SMILES: COc1ccc(C2=NCC(=O)N(C)c3cc(OC)c(-c4cc(OC)ccc4OC)cc32)cc1] | |
| 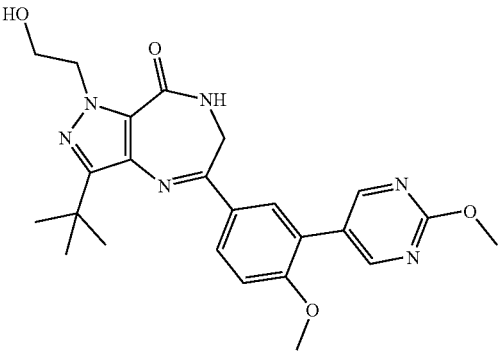 [SMILES: COc1ncc(-c2cc(C3=Nc4c(C(C)(C)C)nn(CCO)c4C(=O)NC3)ccc2OC)cn1] | |
| 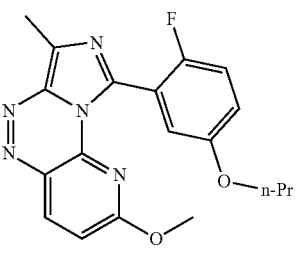 | |
| 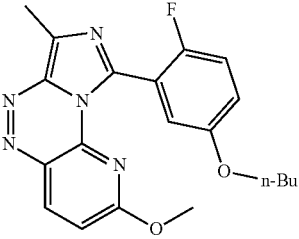 | |

-continued
| Compound | Name |
|---|---|
| 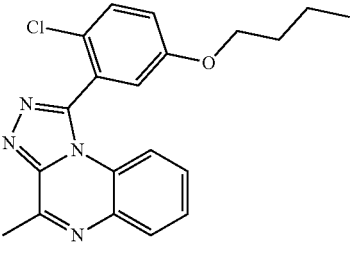 [SMILES: CCCCOc1ccc(Cl)c(-c2nnc3c(C)nc4ccccc4n23)c1] | |
| 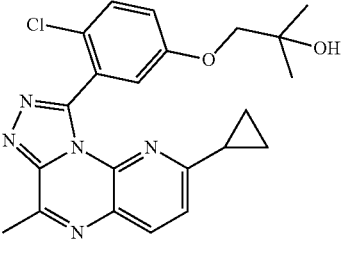 [SMILES: Cc1nc2ccc(C3CC3)nc2n2c(-c3cc(OCC(C)(C)O)ccc3Cl)nnc12] | |
| 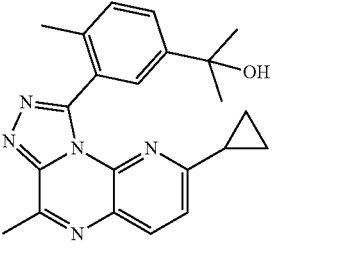 [SMILES: Cc1ccc(C(C)(C)O)cc1-c1nnc2c(C)nc3ccc(C4CC4)nc3n12] | |
| 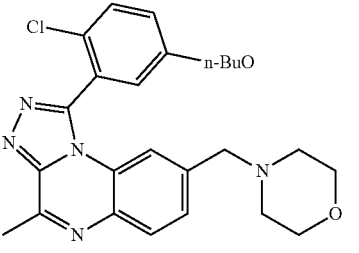 | |
| 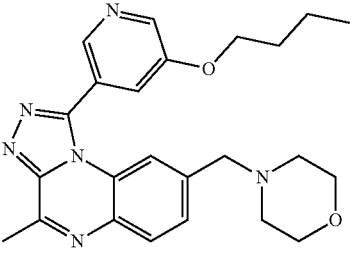 [SMILES: CCCCOc1cncc(-c2nnc3c(C)nc4ccc(CN5CCOCC5)cc4n23)c1] | |
| 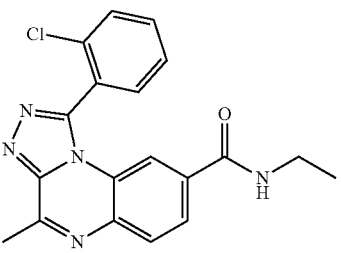 [SMILES: CCNC(=O)c1ccc2nc(C)c3nnc(-c4ccccc4Cl)n3c2c1] | |

| Compound | Name |
|---|---|
| 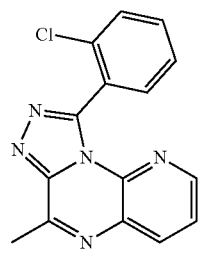 [SMILES: Cc1nc2cccnc2n2c(-c3ccccc3Cl)nnc12] | |
| 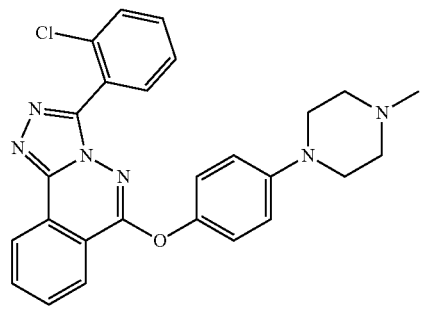 [SMILES: CN1CCN(c2ccc(Oc3nn4c(-c5ccccc5Cl)nnc4c4ccccc34)cc2)CC1] | Lu AF64280 |
| 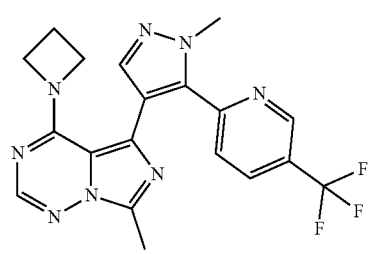 [SMILES: Cc1nc(-c2cnn(C)c2-c2ccc(C(F)(F)F)cn2)c2c(N3CCC3)ncnn12] | PF-05180999 |
| 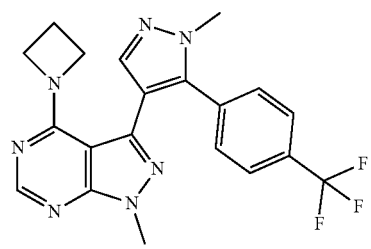 [SMILES: Cn1ncc(-c2nn(C)c3ncnc(N4CCC4)c23)c1-c1ccc(C(F)(F)F)cc1] | |
| 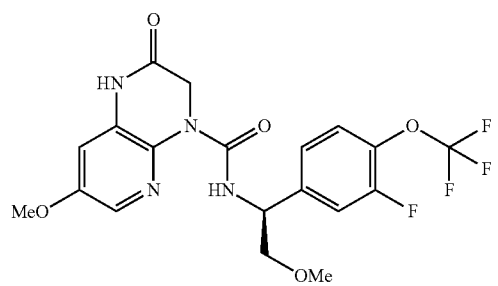 [SMILES: COC[C@@H](NC(=O)N1CC(=O)Nc2cc(OC)cnc21)c1ccc(OC(F)(F)F)c(F)c1] | TAK-915 N-((1S)-1-(3-fluoro-4-(trifluoromethoxy)phenyl)-2-methoxyethyl)-7-methoxy-2-oxo-2,3-dihydropyrido[2,3-b]pyrazine-4-(1H)-carboxamide |
| 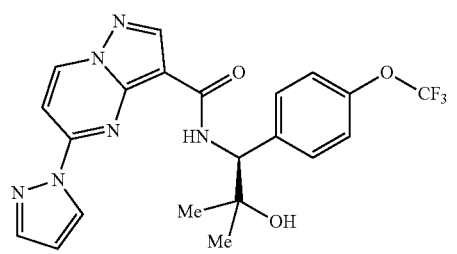 [SMILES: CC(C)(O)[C@@H](NC(=O)c1cnn2ccc(-n3cccn3)nc12)c1ccc(OC(F)(F)F)cc1] | N-(1S)-2-hydroxy-2-methyl-1-(4-(trifluoromethoxy)phenyl)propyl)-5-(1H-pyrazol-1-yl)pyrazolo[1,5-a]pyrimidine-3-carboxamide |

-continued

| Compound | Name |
|---|---|
| | N-(1S)-2-hydroxy-2-methyl-1-(4-(trifluoromethoxy)phenyl)propyl)-5-(4-methyl-1H-1,2,3-triazol-1-yl)pyrazolo[1,5-a]pyrimidine-3-carboxamide |
| | N-(1S)-2-hydroxy-2-methyl-1-(4-(trifluoromethoxy)phenyl)propyl)-5-(3-methyl-1H-1,2,4-triazol-1-yl)pyrazolo[1,5-a]pyrimidine-3-carboxamide |
| | |
| | |
| | ND-7001 3-(8-methoxy-1-methyl-2-oxo-7-phenyl-2,3-dihydro-1H-benzo[e][1,4]diazepin-5-yl)benzamide |

| Compound | Name |
|---|---|
| 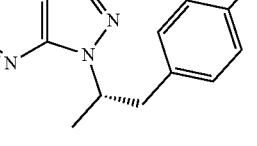 | PDM-631<br>((S)-3-cyclopropyl-6-methyl-1-(1-(4-(trifluoromethoxy)phenyl)propan-2-yl)-1,5-dihydro-4H-pyrazolo[3,4-d]pyrimidin-4-one |
| 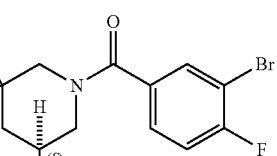 | DNS-8254<br>(5S)-1-[(3-bromo-4-fluorophenyl)carbonyl]-3,3-difluoro-5-{5-methyl-[1,2,4]triazolo[1,5-a]pyrimidin-7-yl}piperidine |
| 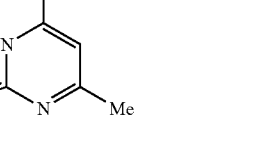 | 1-[2,3-dihydro-1-benzofuran-5-yl)carbonyl]-3-{5-methyl-[1,2,4]-triazolo[1,5-a]pyrimidin-7-yl}piperidine |
| 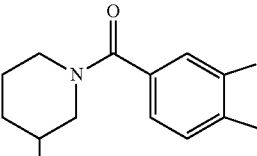 | 6-[(3-{5-methyl-[1,2,4]triazolo[1,5-a]pyrimidin-7-yl}piperidin-1-yl)carbonyl]quinolone |
| 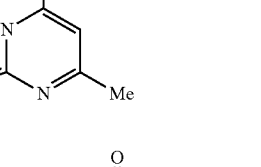 | |

| Compound | Name |
|---|---|
| (structure: 2-chlorophenyl triazolo-pyrido-pyrazine) | |
| (structure: chloro/trifluoroethoxymethyl phenyl triazolo-pyrido-pyrazine) | |
| (structure: pyridyl/n-butoxy triazolo-pyrido-pyrazine) | |
| (structure: adenine with 2-hydroxy-3-nonyl chain) | EHNA (erythro-9-(2-hydroxy-3-nonyl)adenine). |

7. The method of claim 1, wherein said compound is selected from TAK-915 (N-((1S)-1-(3-fluoro-4-(trifluoromethoxy) phenyl)-2-methoxyethyl)-7-methoxy-2-oxo-2,3-dihydropyrido[2,3-b]pyrazine-4-(1H)-carboxamide); ND-7001 (3-(8-methoxy-1-methyl-2-oxo-7-phenyl-2,3-dihydro-1H-benzo[e]-[1,4]diazepin-5-yl)benzamide); PF-05180999 or Lu AF64280; and their pharmaceutically acceptable salts and prodrugs thereof.

8. The method of claim 1, wherein said compound is TAK-915 (N-((1S)-1-(3-fluoro-4-(trifluoromethoxy)phenyl)-2-methoxyethyl)-7-methoxy-2-oxo-2,3-dihydropyrido[2,3-b]pyrazine-4-(1H)-carboxamide), or PF-05180999, or a pharmaceutically acceptable salt or prodrug thereof.

9. The method of claim 1, wherein said compound is BAY 60-7550 (2-(3,4-dimethoxybenzyl)-7-[(2R,3R)-2-hydroxy-6-phenylhexan-3-yl]-5-methylimidazo[5,1-f][1,2,4]triazin-4(3H)-one), ND-7001 (3-(8-methoxy-1-methyl-2-oxo-7-phenyl-2,3-dihydro-1H-benzo[e]-[1,4]diazepin-5-yl) benzamide), PF-05180999 as defined in claim 6, or Lu AF64280 as defined in claim 6, or a pharmaceutically acceptable salt or prodrug thereof.

10. The method of claim 1, wherein said subject has previously suffered a myocardial infarction, a heart failure, or is predisposed to tachycardia.

11. The method of claim 1, wherein said subject is suffering from, or at risk of suffering from, heart failure, CPVT or long QT syndrome.

12. The method of claim 10, wherein said subject is selected from any of the following:
a subject previously diagnosed with, and/or treated for, a cardiac arrhythmia;
a subject who has an implanted cardiac defibrillator (ICD); or
a subject undergoing long term treatment for a cardiac arrhythmia.

13. The method of claim 12, wherein said subject has an implanted cardiac defibrillator (ICD) and is undergoing treatment with an anti-arrhythmic drug.

14. The method of claim 13, wherein said anti-arrhythmic drug is a $\beta_1$-selective beta-blocker.

15. The method of claim 1, wherein said subject is a human.

16. The method of claim 1, wherein said method additionally comprises the step of administering to said subject one or more cardiovascular drugs.

17. The method of claim 16, wherein said cardiovascular drug is selected from the group consisting of a drug for the treatment of hypertension, heart failure, arrhythmia and/or post infarction myocardial reperfusion syndrome.

18. The method of claim 17, wherein said drug is selected from any of the following: beta-blockers, calcium antagonists, ACE-inhibitors, ATII/-blockers and anti-arrhythmic drugs.

19. The method of claim 18, wherein the beta-blocker is a $\beta_1$-selective beta-blocker.

20. The method of claim 19, wherein said $\beta_1$-selective beta-blocker is Metoprolol.

21. The method of claim 1, wherein said subject is a human and said compound is administered at a daily dose of 1 mg to 600 mg.

* * * * *